(12) United States Patent
Korkuch et al.

(10) Patent No.: US 12,233,224 B2
(45) Date of Patent: Feb. 25, 2025

(54) PERSISTENT PERFUSION SHEATH

(71) Applicant: ABIOMED, Inc., Danvers, MA (US)

(72) Inventors: Christopher Nason Korkuch, Danvers, MA (US); Caitlyn Hastie, Danvers, MA (US); Glen Robert Fantuzzi, Danvers, MA (US); Robert Fishman, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 200 days.

(21) Appl. No.: 17/964,089

(22) Filed: Oct. 12, 2022

(65) Prior Publication Data

US 2023/0158277 A1 May 25, 2023

Related U.S. Application Data

(63) Continuation of application No. 16/723,253, filed on Dec. 20, 2019, now Pat. No. 11,497,894.
(Continued)

(51) Int. Cl.
*A61M 25/00* (2006.01)
*A61M 25/06* (2006.01)
(Continued)

(52) U.S. Cl.
CPC ........ *A61M 25/0662* (2013.01); *A61M 25/10* (2013.01); *A61M 60/13* (2021.01);
(Continued)

(58) Field of Classification Search
CPC .. A61M 2025/0079; A61M 2025/1097; A61M 25/007; A61M 25/0071
See application file for complete search history.

(56) References Cited

U.S. PATENT DOCUMENTS 5,368,579 A    11/1994   Sandridge
8,795,253 B2   8/2014    Moshinsky et al.
(Continued)

FOREIGN PATENT DOCUMENTS

CN    103974670 A    8/2014
CN    204275256 U    4/2015
(Continued)

OTHER PUBLICATIONS

Office Action from corresponding Japanese Patent Application No. 2021-535532 dated Aug. 14, 2024 (6 pp.).
(Continued)

*Primary Examiner* — Deanna K Hall
(74) *Attorney, Agent, or Firm* — Botos Churchill IP Law LLP

(57) ABSTRACT

A persistent perfusion sheath assembly can be used for the passage of an intravascular medical device while maintain a flow passage in the vessel. The sheath assembly passes through an arteriotomy and can include a first lumen configured for the passage of a medical device, a second lumen configured to allow a flow of fluid from a location in the blood vessel upstream of the arteriotomy to a location downstream of the arteriotomy. The sheath assembly can further include a stylet, a sleeve or an additional sheath configured to selectively open and close the flow of blood between upstream and downstream of the arteriotomy. The sheath assembly can further include a closure device distal of the arteriotomy, the closure device configured to control blood flow through the arteriotomy.

28 Claims, 24 Drawing Sheets

Related U.S. Application Data

(60) Provisional application No. 62/783,554, filed on Dec. 21, 2018.

(51) Int. Cl.
*A61M 25/10* (2013.01)
*A61M 60/13* (2021.01)
*A61M 60/216* (2021.01)
*A61M 60/865* (2021.01)
*A61F 2/958* (2013.01)
*A61M 60/135* (2021.01)

(52) U.S. Cl.
CPC ........ *A61M 60/216* (2021.01); *A61M 60/865* (2021.01); *A61F 2/958* (2013.01); *A61M 2025/0687* (2013.01); *A61M 2025/1097* (2013.01); *A61M 60/135* (2021.01)

(56) References Cited

U.S. PATENT DOCUMENTS

| | | | |
|---|---|---|---|
| 10,729,457 | B2 | 8/2020 | Lenker et al. |
| 2002/0107506 | A1 | 8/2002 | McGuckin et al. |
| 2013/0072941 | A1 | 3/2013 | Tan-Malecki et al. |
| 2013/0085381 | A1 | 4/2013 | Comerota et al. |
| 2013/0289527 | A1 | 10/2013 | Ravenscroft |
| 2014/0018619 | A1 | 1/2014 | Khoury |
| 2017/0049947 | A1 | 2/2017 | Corbett et al. |
| 2017/0164605 | A1 | 6/2017 | Tillman et al. |
| 2018/0104402 | A1 | 4/2018 | Ahmad et al. |

FOREIGN PATENT DOCUMENTS

| | | |
|---|---|---|
| CN | 107072666 A | 8/2017 |
| CN | 107405474 A | 11/2017 |
| CN | 107412892 A | 12/2017 |
| CN | 107735140 A | 2/2018 |
| EP | 0951309 A1 | 10/1999 |
| JP | 2018523541 A | 8/2018 |
| WO | 2006023203 A1 | 3/2006 |
| WO | 2012061657 A2 | 5/2012 |
| WO | 2013019947 A2 | 2/2013 |
| WO | 2016040579 A1 | 3/2016 |
| WO | 2016183123 A1 | 11/2016 |
| WO | 2017031243 A1 | 2/2017 |

OTHER PUBLICATIONS

First Examination Report issued in corresponding Indian Patent Application No. 202117031865, mailed Jan. 6, 2023, 6 pages.
First Office Action and Search Report issued in corresponding Chinese Patent Application No. 2019800911316, mailed Dec. 19, 2022, 33 pages.
Office Action issued in Japanese Patent Application No. 2021535532 dated Nov. 8, 2023 (7 pp.).
Office Action from corresponding Chinese Patent Application No. 2019800911316 dated Sep. 1, 2023 (13 pp.).
International Search Report for Application No. PCT/US2019/068031 dated Jul. 6, 2020.
Partial Search Report and Written Opinion for Application No. PCT/US2019/068031 dated May 15, 2020.
Search Report for European Patent Application No. 19842971.4 dated Dec. 17, 2024 (12 pp.).

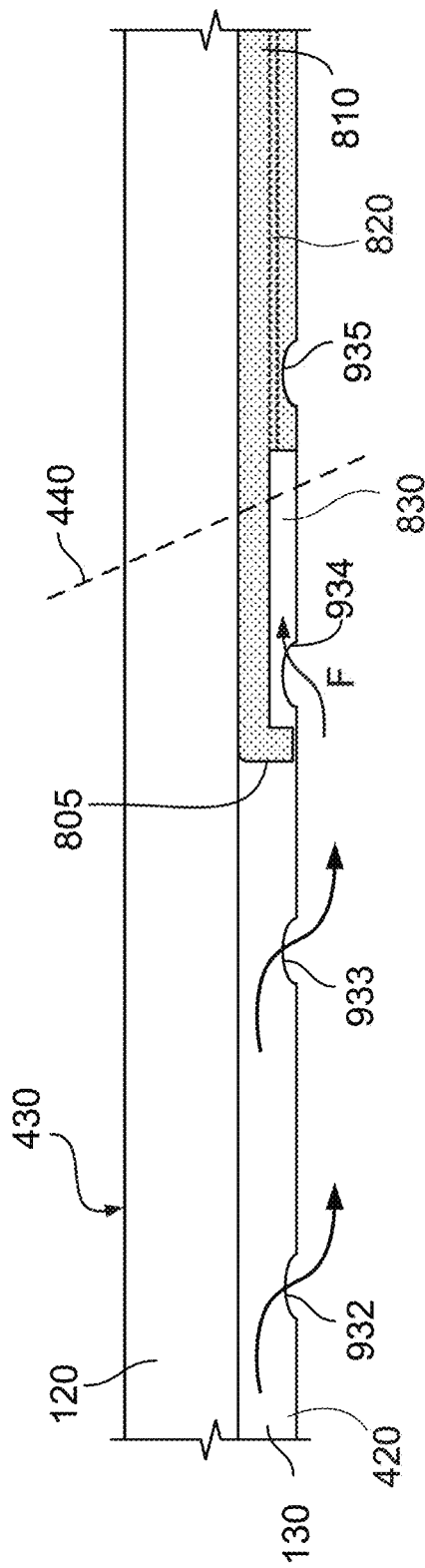
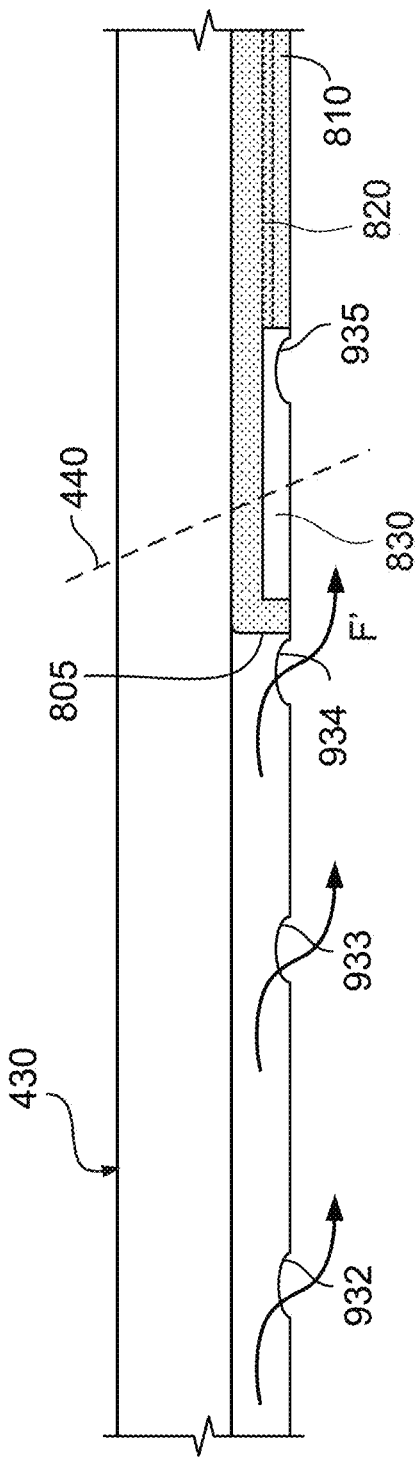
FIG. 9A
FIG. 9B

PERSISTENT PERFUSION SHEATH

CROSS-REFERENCE TO RELATED APPLICATIONS

This application is a continuation of U.S. application Ser. No. 16/723,253, filed on Dec. 20, 2019, now U.S. Pat. No. 11,497,894, which application claims the benefit of Application Ser. No. 62/783,554, filed Dec. 21, 2018, the disclosures of which are hereby incorporated herein by reference.

BACKGROUND OF THE INVENTION

Intravascular medical devices such as percutaneous pumps (e.g. the Impella 2.5™ system by Abiomed, Inc., Danvers, Massachusetts), catheters, guidewires, balloon angioplasty catheters, delivery sheaths, and implant delivery systems are commonly used during minimally invasive procedures in the cardiovascular, cerebrovascular and peripheral vascular systems. Such medical devices can be introduced into a patient in various ways. Blood pump assemblies are introduced surgically or percutaneously during a cardiac procedure through the vascular system. Such intravascular procedures are minimally invasive. In one common approach, pump assemblies are inserted by a catheterization procedure through the femoral artery using a sheath, such as a peel-away introducer sheath. The femoral artery is commonly used in such procedures primarily due to ease of access. The sheath is inserted into the femoral artery through an arteriotomy (access site in the artery) to create an insertion path for the pump assembly. A portion of the pump assembly is then advanced through an inner lumen of the introducer sheath and into the artery. Once the pump assembly has been inserted, the introducer sheath is removed, for example by being peeled away. A repositioning sheath can then be advanced over the pump assembly and into the arteriotomy.

The introducer sheath must be large enough in diameter to accommodate the intravascular device, e.g., the blood pump. To date, the smallest available heart pump is the Impella 2.5 percutaneous heart pump, which has a motor diameter of about 12 Fr. The sheath must therefore be at least 13 Fr in order to introduce the Impella 2.5 pump. Other pumps and devices are larger than Impella 2.5, for example the Impella CP pump with a motor diameter of about 14 Fr, and the Impella 5.0 pump with a motor diameter of about 21 Fr or larger, depending on the type of device. An even larger sheath would be needed for such devices.

While existing introducer sheaths are generally functional for device insertion, they have drawbacks. For example, due to its size, the introducer sheath can block the cross sectional area of the artery, and thereby occlude the artery, which can drastically restrict down-stream blood flow. Restricted blood flow can be problematic for a number of reasons, including causing intermittent claudication, leg numbness/weakness and limb ischemia which may even result in loss of the limb.

Conventionally, limb ischemia is known as a "distal perfusion" issue in the sense that it often occurs downstream from the insertion site of the device. In the present disclosure, a "distal" element is the part of the element located farthest away from the clinician and "proximal" is the part of the element that is closest to the clinician. In the case of a sheath deployed inside a patient, the sheath end that is deployed inside the body of the patient is the "distal" end, whereas the handle or end held by the clinician located outside the patient is the "proximal" end.

For relatively large medical devices (e.g. with a maximum outer diameter equal to or greater than 12 Fr), the introducer sheath (or repositioning sheath) used in combination with the medical device has an outer diameter which is substantially similar in size to an inner diameter of the artery or vessel in which the sheath is positioned. This match between the outer diameter of the sheath and inner diameter of the artery or vessel prevents blood from flowing from a location upstream of the arteriotomy to a location downstream of the arteriotomy. Moreover, for these relatively large medical devices, the introducer sheath (or repositioning sheath) used in combination with the medical device also requires a large access site, which may be difficult to close, or to control bleeding at when inserting or withdrawing the sheath. The size of a medical device (e.g., relatively large, or relatively small), and accordingly whether an introducer sheath or repositioning sheath is considered relatively large, can depend on a particular patient's anatomy.

Other drawbacks may include excessive bleeding at the arteriotomy during insertion or removal of the sheath, which can result in blood loss for the patient, and weakening of the patient. This is normally treated by using closure devices such as collagen injections, sutures or staples. But these types of closure devices can be challenging to use when blood flow has not yet been adequately stopped, and floods the access site being closed. Moreover, these types of closure devices generally require additional tools or steps and therefore require time effectively close.

The size of an introducer sheath and its impact on the patient may be complicated by patient anatomy (e.g. heavy stenosis and small vessels) and condition (e.g. shock, vasospasm, patient on vasopressors with constricted vessels) which can limit the size of introducer that can be used to gain access. In the case of vasospasm, even an appropriately sized sheath to the original vessel diameter will fill the entire contracted vessel. Accordingly, for some patients a very small sheath, e.g., 6 Fr, can be too large and lead to the same occlusion and access bleed concerns as a 12 Fr sheath in another patient.

In general, the drawbacks noted above are more pronounced for long-term vascular procedures. Certain procedures in the catheter lab are short term and therefore present less risk, for example, typically only require at most 4-5 hours, with physicians periodically checking for distal (limb) perfusion. However, even in short-term situations physicians may forget to confirm the patient has adequate distal perfusion from the device, or miss warning signs of inadequate limb perfusion. Additionally, certain patients may be transferred to the ICU with introducer sheaths or repositioning sheaths staying in the patient for longer periods of times ranging from 1-14 days. In such instances, the problems of vessel occlusion and associated limb ischemia, and access site bleeding can be exacerbated.

A known intervention to an occluded femoral artery would be a fem-to-fem bypass for arterial revascularization. The technique includes gaining access, usually with a small sheath (e.g. with a 4 Fr catheter) to gain access to the opposite leg of the main access site, using a similar sheath to gain access to a distal portion of the same leg of the main access site, and connecting the two sheaths together to allow perfusion to the patient's main access leg using blood flow from the opposite leg. However such an intervention procedure comes with other risks, including difficulty in gaining access to the distal portion of the blocked leg (due to lack of flow, pressure, pulsatility, or a combination of these), additional allocation of resources (time, use of materials and extra components), increased risk of infection, and other risks associated with multiple access sites. Another potential intervention would be to use ECMO. However, such an intervention procedure comes with issues similar to those faced for fem-fem bypass, and other challenges.

A potential intervention to address an access site with undesirably large bleeding would be to use collagen or a metallic clip or suture to close the access site. However, such an intervention is usually unplanned and rushed, and can be difficult to visualize in view of the ongoing bleeding at the access site itself.

BRIEF SUMMARY OF THE INVENTION

The systems, method and devices described herein provide an improved sheath for delivering an intravascular device but also restoring perfusion of blood within a patient distal to the device, for example in the lower extremities distal of an occluded vessel. Advantages may be realized. In some implementations, distal perfusion may be achieved without removal of the sheath. Distal perfusion may be achieved with limited or reduced number of access sites (in contrast to a fem-to-fem bypass system). The systems, method and devices described herein restore the circulation of blood in the vasculature of a patient (usually the lower extremities) with minimal additional steps. Also disclosed herein are means for determining the position of an arteriotomy along the length of a catheter to help achieve more efficient positioning, as well as means for positioning a stylet relative to the location of the arteriotomy.

The systems, methods and devices described herein further provide a sheath with an integrated closure device which prevents unwanted bleeding at the access site without the need for an additional medical procedure (collagen injection or suture), or without the need for sheath removal. In some embodiments, the integrated closure device is positioned upstream of the arteriotomy. In other embodiments, the integrated closure device is positioned at the arteriotomy. In some embodiments, the integrated closure device is deployed by inflation. In other embodiments, the integrated closure device is deployed by a mechanical expansion.

According to an aspect of the present disclosure, there is provided a sheath system having a sheath with a lumen through which a medical device can be inserted, and a mechanism configured to allow a flow of fluid from the blood vessel either through or around the sheath, without being substantially blocked from reaching areas of the patient downstream of the sheath. The mechanism may deploy a second lumen, one or more apertures, an expandable portion, or other means for allowing blood flow from a portion of the artery upstream of the sheath to a portion of the artery downstream of the device.

In some embodiments, the sheath assembly is configured with a second lumen that permits blood to flow around the sheath. For example, the second lumen may run alongside the sheath (e.g., a side-rigger), or may run inside the sheath. The lumen has a first end with a first an inlet port and a second end with an outlet port, where the inlet is positioned at or near the distal end of the sheath and the outlet is positioned on an opposite side of the sheath, thereby permitting blood to enter the inlet end and exit the lumen on the opposite side of the sheath. A stylet may be provided and configured so as to selectively open and close the second lumen along the longitudinal axis when the first end of the sheath body is positioned within the blood vessel and the second end of the sheath is external to the patient, so as to prevent blood from exiting the vessel altogether.

In other adaptations, the sheath assembly is configured with apertures in the sheath itself, and a covering for those apertures, which covering can be removed to allow blood to flow through the apertures. The covering may include a second outer sheath that is retractable (e.g., by the physician) to expose the apertures in the sheath to permit blood to flow into the sheath and out through its apertures to reach downstream vasculature. The covering may include an inner device such as a stylet positioned within the sheath, and configured so that it is retracted to expose the apertures in the sheath.

In other adaptations, one or more channels or other components are provided external to the sheath surface that permit blood to flow past the sheath. For example, one or more balloons may be used to facilitate blood flow past the sheath. In some arrangements, a balloon is affixed to the external surface of the sheath and, upon inflation, expands the blood vessel in the vicinity of the sheath to permit blood to flow around the outside of the sheath. A second sheath downstream of the first sheath may be used to facilitate blood flow from upstream of the first sheath to downstream of the first sheath. A sheath with an expandable distal end may be used to increase a diameter of the artery in which the sheath is placed, and permit blood to flow into the distal end of the sheath, through the expandable distal end and into the artery downstream of expandable distal end.

Also contemplated are methods for inserting a medical device into a patient through a sheath system, such as percutaneous methods for inserting a medical device into a blood vessel of a patient. The methods comprise inserting a sheath assembly through a skin puncture into an artery at an arteriotomy, and passing a medical device through the sheath assembly. The methods further comprise manipulating the sheath assembly to allow flow of blood between a location upstream of the arteriotomy and a location downstream of the arteriotomy while simultaneously ensuring hemostasis through the arteriotomy. At least one benefit of the methods is to increase blood flow between locations upstream and downstream of the arteriotomy, and controlling blood loss at the access site. Large diameter pumps and pumps with large components may be suited to use with the systems.

According to another aspect of the present disclosure, methods are provided for deploying a sheath within a blood vessel, and delivering a device through the sheath with minimal or no downstream ischemia. In some adaptations, methods are provided for percutaneously inserting a medical device (for example a large diameter blood pump) into a blood vessel of a patient by inserting a sheath assembly that can facilitate delivery of the device to its intended location in the vasculature without significantly occluding the blood vessel. The methods can be used with a sheath having a diameter substantially equal to a cross-sectional diameter of the artery located beneath the arteriotomy, such that the sheath is sufficiently wide to extend across the diameter of the artery in that location. The methods further include passing a medical device through the sheath assembly and permitting flow of blood between a location upstream of the arteriotomy and a location downstream of the arteriotomy, to reach downstream regions of the patient, while simultaneously ensuring hemostasis through the arteriotomy. In that respect, the method operates so as to allow blood to flow without being blocked by the sheath. Another benefit of this method is to enable blood flow between locations upstream and downstream of the arteriotomy for sheaths which are relatively large compared to a cross-section of the artery, while preventing excessive blood loss at the access site.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 9A shows a longitudinal cross section of the sheath assembly of FIG. 6 during use to determine if blood from the vessel is flowing through the second lumen of the sheath;

FIG. 9B shows a longitudinal cross section of the loaded sheath of FIG. 6 during use once the stylet has been sufficiently retracted to ensure flow of blood in the vessel through the second lumen of the sheath;

DETAILED DESCRIPTION

To provide an overall understanding of the systems, method, and devices described herein, certain illustrative embodiments will be described. Although the embodiments and features described herein are specifically described for use in connection with a percutaneous heart pump system, it will be understood that the components and other features outlined below may be combined with one another in any suitable manner and may be adapted and applied to other types of medical devices such as stents, transcatheter aortic valve replacement (TAVR) delivery systems, cardiac therapy and cardiac assist devices, including balloon pumps, cardiac assist devices implanted using a surgical incision, and other vascular devices.

The systems, methods and devices of the present disclosure provide a perfusion sheath assembly for insertion into a blood vessel of a patient. The sheath assembly comprises a lumen configured for the passage of a medical device. The sheath assembly further comprises a mechanism configured to allow a flow of fluid within the blood vessel without being substantially blocked from reaching areas of the patient downstream of the sheath. The sheath assembly further comprises a closure device configured to prevent a flow of fluid from the blood vessel out the arteriotomy.

Figure 1A:
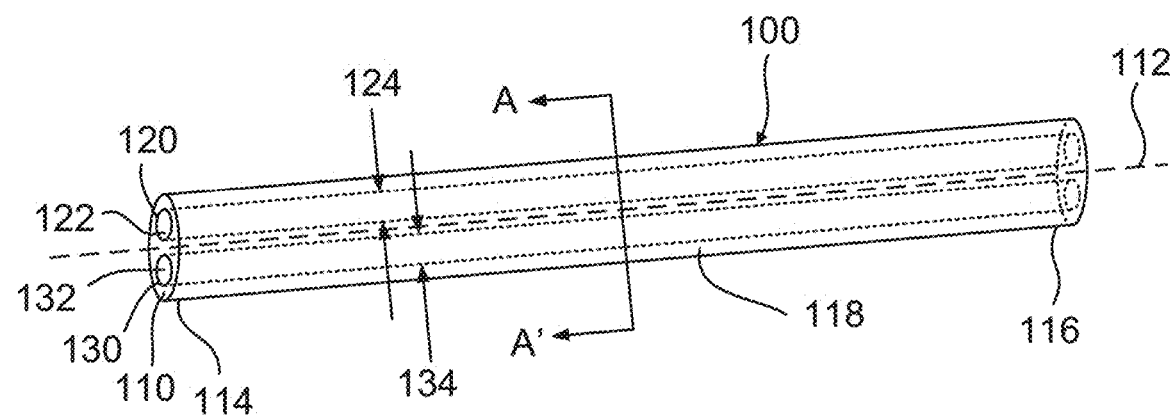
FIG. 1A shows an isometric view of a representative persistent perfusion sheath according to an implementation of the present disclosure.

FIG. 1A shows an isometric view of an illustrative persistent perfusion sheath 100 according to certain implementations of the present disclosure. The perfusion sheath 100 is suitable for insertion into the arteriotomy of a patient, such as the femoral artery. The sheath 100 comprises a sheath body 110 extending along a longitudinal axis 112. The sheath body 110 has a distal end 114, a proximal end 116, and an outer surface 118. In certain implementations, the sheath body 110 is tubular with a circular cross section, however the sheath body 110 can be of any shape and configuration. The sheath body 110 comprises a first lumen 120 extending between the distal end 114 and the proximal end 116 of the sheath body 110. The sheath body 110 further comprises a second lumen 130 extending between the distal end 114 and the proximal end 116 of the sheath body 110. The first lumen 120 has an inner surface 122 and the second lumen 130 has an inner surface 132. The first lumen 120 is open for the passage of a medical device such as a percutaneous pump (not shown), and the second lumen 130 is open to allow the flow of fluid from a blood vessel therethrough. An example of such a percutaneous pump is the Impella 2.5™ system (Abiomed, Inc., Danvers, Massachusetts). Such a pump generally comprises a catheter body with a pump head at a distal end of the catheter body and a handle at a proximal end of the catheter body. It will be understood that while a percutaneous heart pump is described herein, any other percutaneous or intravascular medical device can be used in conjunction with the present disclosure, for example by delivering such a device through a sheath according to the disclosure herein.

In some implementations, the first lumen 120 has a circular cross section with a first diameter 124. The first lumen 120 is dimensioned such that a medical device is able to traverse the length of the first lumen 120, i.e. the diameter 124 of the first lumen 120 is suitably larger than the largest diameter of the medical device. In certain implementations, the first diameter 124 need only be marginally larger than the catheter body of the medical device. Further, in some implementations, the diameter 124 is selected such that the inner surface 122 of the first lumen forms an interference fit with an outer surface of a medical device inserted into the first lumen 120 while allowing longitudinal movement of the device in the first lumen 120. Such an interference fit ensures a minimal or no gap exists between the medical device and the inner surface 122. This would guard against the passage of fluid in any space that develops between the inner surface 122 of the first lumen 120 and the medical device which may coagulate and block the first lumen 120 of the sheath 100. In certain implementations, the second lumen 130 has a circular cross section with a second diameter 134. However it will be understood that while FIG. 1A depicts the first and second lumens 120, 130 as having a circular cross section, these lumens may have any cross sectional shape.

Figure 1B:
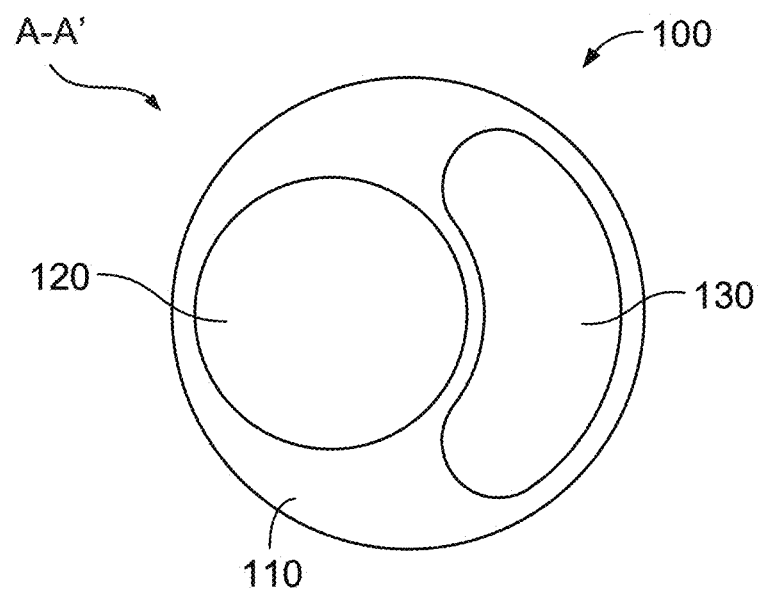
FIG. 1B shows a transverse cross section the perfusion sheath of FIG. 1A according to an implementation of the present disclosure.

FIG. 1B shows the cross section of the perfusion sheath 100 taken along the cut line A-A' in FIG. 1A. The cross section shows the sheath body 110, the first lumen 120 and the second lumen 130. In this implementation, the first lumen 120 has a circular cross section, while the second lumen 130 has a bean shape cross section. It will be understood that the shapes of the first lumen 120 and the second lumen 130 are such that they complement each other so that their combined cross sectional areas closely match the cross sectional area of the sheath body 110, without compromising on the mechanical strength of the sheath body 110. This ensures maximum utility of the available space within the sheath body 110.

Figure 2A:
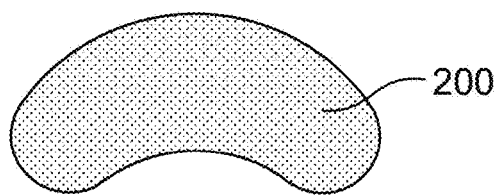
FIG. 2A shows a transverse cross section of a stylet according to an implementation of the present disclosure.
Figure 2B:
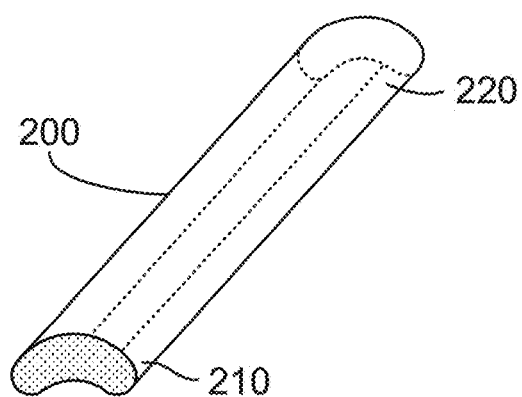
FIG. 2B shows an isometric view of the stylet of FIG. 2A.

FIGS. 2A and 2B illustrate a stylet 200 that is configured to be inserted into the second lumen 130 of the perfusion sheath 100. Insertion and retraction of the stylet 200 into and from the second lumen 130 allows for the second lumen 130 to be selectively closed and opened, respectively, as necessary. For example, during vasospasms the blood vessels in the arteriotomy of a patient may be constricted such that the perfusion sheath 100 may fully block the vessel thereby stopping the flow of blood. In such a situation, the stylet 200 can be partially or wholly removed from the second lumen 130 so as to provide a passageway within the sheath body 110 for the flow of blood in the blood vessel. The stylet 200 has a cross sectional shape that matches that of the second lumen 130 such that it has an interference fit with the inner surface 132 of the second lumen 130 when the stylet 200 is inserted into the second lumen 130. The stylet 200 has the same cross section throughout its length. The stylet 200 is at least as long as the longitudinal length of the sheath body 110. When fully inserted into the second lumen 130, the distal end 210 of the stylet 200 aligns with the distal end 114 of the sheath body 110 and the proximal end 220 of the stylet 200 aligns with the proximal end 116 of the sheath body 110. In the illustrated examples of FIGS. 1A, 1B and 2, the stylet 200 has a bean shape cross section to match the bean shaped cross section of the second lumen 130. However it will be understood that the stylet can take on any cross sectional shape necessary to match that of the second lumen 130. In other implementations, the stylet 200 may be longer than the sheath body 110 such that the proximal end 220 does not align with the proximal end 116 of the sheath body 110. In some implementations the stylet 200 may comprise more than one member. In other implementations, the stylet 200 may comprise an inner lumen running through its length, as will be discussed in the sections that follow. In further implementations, the stylet 200 can be completely removed from the second lumen 130 so as to insert a guidewire to maintain the position of the arteriotomy and target vessel.

The sheath body 110 comprises a flexible material. The flexible material is an elastic material with an elastic modulus of about 1.6 ksi. Ksi is a unit of pressure, representing thousands of pounds per square inch. In some implementations, the flexible material is a material with a yield strain of about 200%. In some implementations, the flexible material contains a radiopaque filler such as bismuth oxychloride or barium sulfate in concentrations of 5% to 40% by weight. In certain implementations, the flexible material comprises any one of: ethylene-vinyl acetate (EVA), styrene-butadiene copolymer (SBC), synthetic rubber, or any other elastomer.

The stylet 200 comprises a rigid material. The rigid material is a polyethylene or polyurethane material with an elastic modulus of about 40 ksi. In some implementations the rigid material contains a radiopaque filler such as bismuth oxychloride or barium sulfate in concentrations of 5% to 40% by weight. In some implementations, the rigid material is any one of a high-density polyethylene (HDPE) material, a medium-density polyethylene (MDPE) material, a low-density polyethylene (LDPE) material, polyether ether ketone (PEEK), and a polyether block amide (such as PEBAX). In certain implementations, the rigid material is a crack-resistant material. In some implementations, the rigid material may also be a material with a low coefficient of friction.

Figure 3:
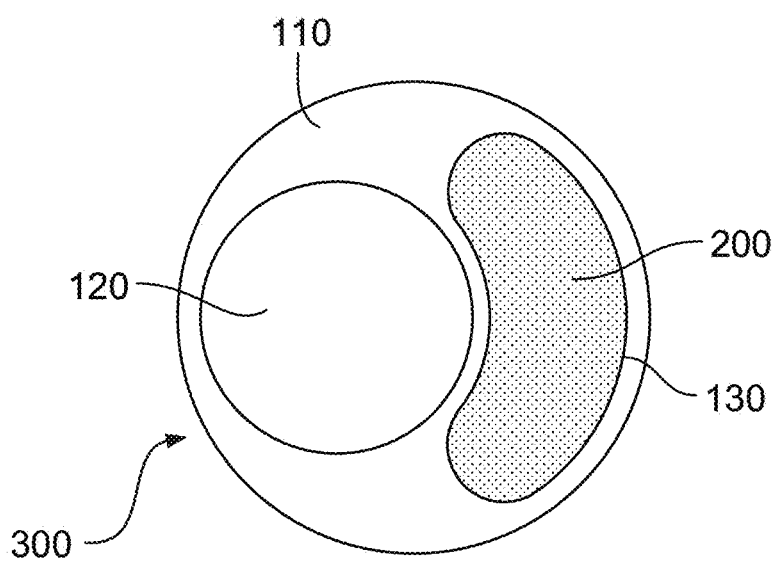
FIG. 3 shows a transverse cross section of the persistent perfusion sheath of FIG. 1 loaded with the stylet of FIG. 2.

FIG. 3 shows a perfusion persistent sheath assembly 300 according to an implementation of the present disclosure. Sheath assembly 300 comprises the persistent sheath 100 as shown in FIGS. 1A and 1B where the sheath body 110 has a first lumen 120 for the passage of a medical device (not shown) and a second lumen 130 for the flow of fluid from an arteriotomy of a patient. FIG. 3 also shows the second lumen 130 closed by the stylet 200 of FIGS. 2A and 2B when the stylet 200 is inserted into the second lumen 130 via an interference fit between the outer surface of the stylet 200 and the inner surface 132 of the second lumen 130. In this manner, the stylet 200 seals the second lumen 130 of the sheath 100 when fully inserted in the second lumen 130. The stylet 200 can be inserted or retracted from the second lumen 130 to selectively control the flow of fluid through the second lumen 130. For example, when flow of fluid through the second lumen 130 is desired, the stylet 200 can be wholly or partially retracted within the second lumen 130. Conversely, when it is required to reduce or block the flow of fluid through the second lumen 130, the stylet 200 at least partially or completely inserted into the second lumen 130.

Figure 4:
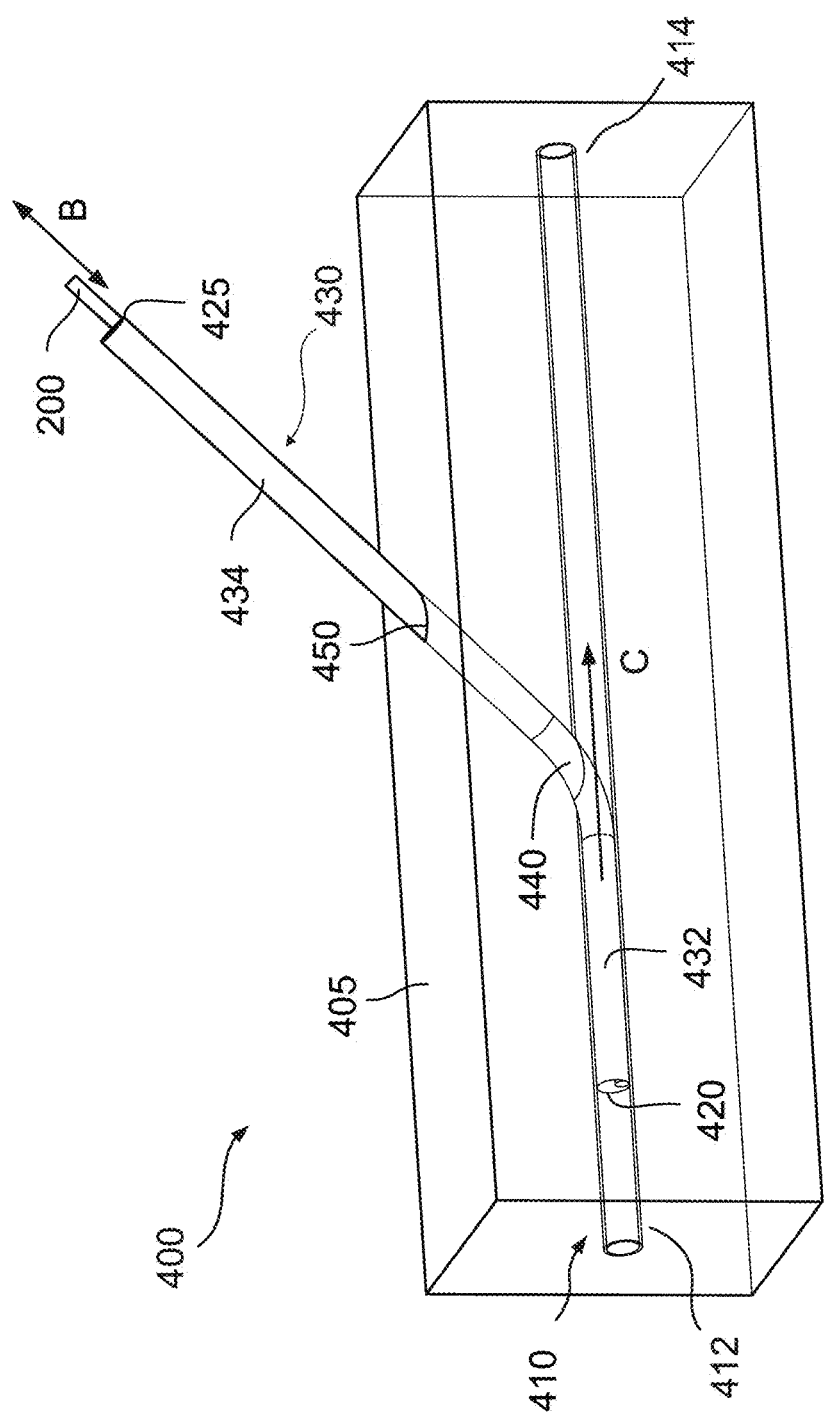
FIG. 4 shows an isometric view of a representative access setup using the persistent perfusion sheath assembly of FIG. 3.

FIG. 4 shows an isometric view 400 of a representative access setup using a loaded sheath assembly 430 similar to sheath assembly 300 in FIG. 3. The sheath assembly 430 has a sheath body 110 comprising a first lumen 120 and a second lumen 130. FIG. 4 shows the body tissue 405 of a patient and a target vessel 410 having an upstream end 412 and a downstream end 414. FIG. 4 also shows a skin insertion site 450 and an arteriotomy 440 where the sheath assembly 430 is inserted into the target vessel 410. The sheath body 110 bends as it enters the arteriotomy of 440. This bend is critical for the selective control of blood flow in the target vessel 410, as will be discussed in the sections that follow. The sheath assembly 430 comprises a proximal end 425 and a distal end 420. When inserted into the vessel 410, the sheath assembly 430 has a first portion 432 (a distal portion) that resides in the vessel 410 of the patient and a second portion 434 (a proximal portion) that is outside the vessel 410. As shown in FIG. 4, the sheath body 110 completely fills the target vessel 410. The sheath assembly 430 is loaded with a stylet 200 (per FIG. 2) which is positioned in the second lumen 130 of the sheath body 110. The stylet 200 can be inserted or retracted from the second lumen 130 by moving the stylet 200 relative to the sheath body 110 as indicated by arrow B in FIG. 4 to control the flow of fluid (e.g. blood) from the distal end 412 to the proximal end 414 in vessel 410 (fluid flow indicated by arrow C from upstream to downstream in FIG. 4). In certain implementations, a hub (not shown) may be coupled to the proximal end 425 of the sheath assembly 430. In other implementations, the first lumen 120 or the second lumen 130 or both may be configured with an elastomer valve.

In some implementations, a flexible atraumatic tip having at least one internal lumen and an open distal end is attached to the distal end 420 of the sheath assembly 430. Here the first and second lumens 120, 130 of the sheath assembly 430 are in fluid communication with the internal lumen of the tip such that a continuous passageway is formed from the distal end 420 of the sheath assembly 430 to the distal end of the tip. In some implementations, the tip comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%. In certain implementations, the inner surface of the tip may be slightly tapered such that the inner diameter is larger at the proximal end than at the distal end of the tip. This creates a slight interference fit with the smallest diameter on the medical device 100 and stylet 200. This forms a slight interference with the medical device 100 and the stylet 200, and helps seal any fluid or blood from entering the first and second lumens 120, 130. In other implementations, the outer surface of the tip is also tapered towards the distal end such that the outer diameter is larger at the proximal end than at the distal end. In certain implementations, the distal end of the tip terminates at a leading edge having a radius to facilitate smooth insertion of the sheath assembly 430 into the vasculature of a patient. The tip is highly resilient and will not exhibit permanent deformation (such as flaring or splitting).

Figure 5A:
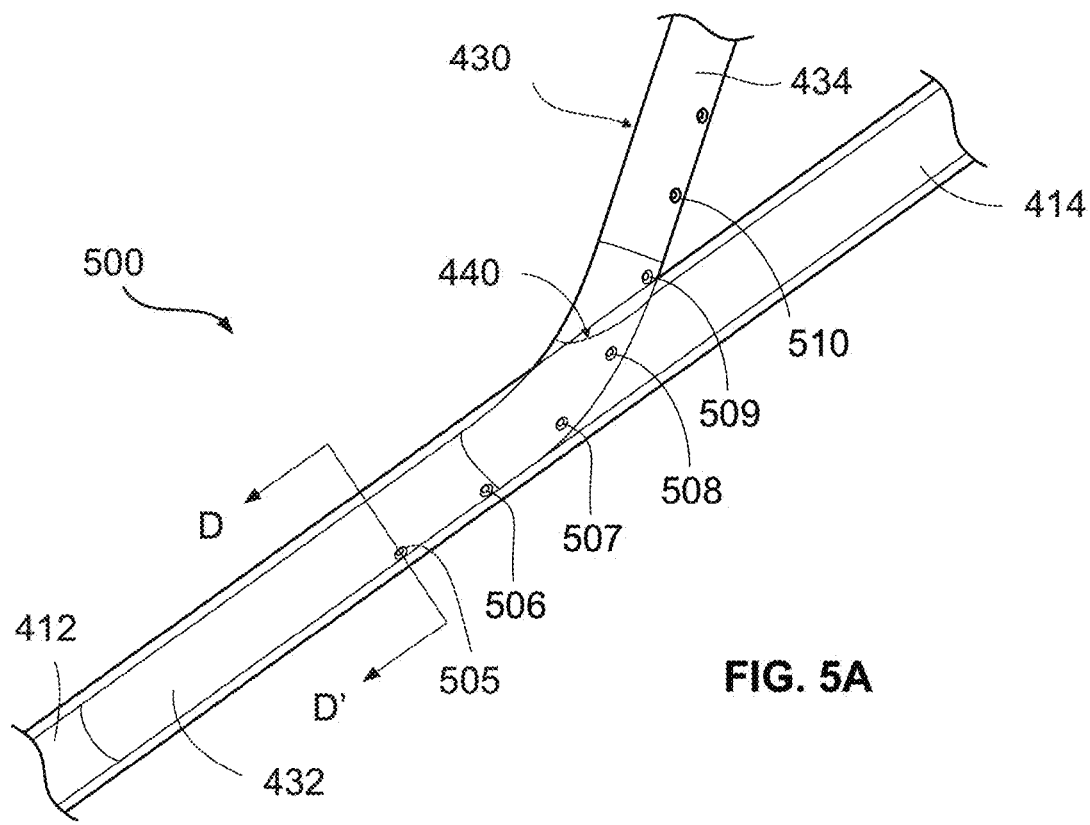
FIG. 5A shows an isometric view of the loaded sheath of FIG. 3 inserted into a blood vessel.

FIG. 5A illustrates the sheath assembly 430 in the vicinity of the arteriotomy 440 of the patient. In FIG. 5A apertures 505-509 are formed along the length of the sheath body 110. These apertures 505-509 terminate in the second lumen 130. The apertures 505-509 are formed along the length of the sheath body 110 such that they are located substantially along the bend of the sheath assembly 430 as it transitions from the insertion angle at the arteriotomy 440 to a position where the sheath lays axial with the vessel 410. When the sheath assembly 430 is positioned in the vessel 410, at least some of the apertures 505-509 formed in the sheath body 110 will be in direct fluid communication with the second lumen 130 so as to allow fluid flowing in the second lumen to exit the sheath body 110 and flow towards the end 414 of the vessel 410 as indicated by arrow C in FIG. 4.

Figure 5B:
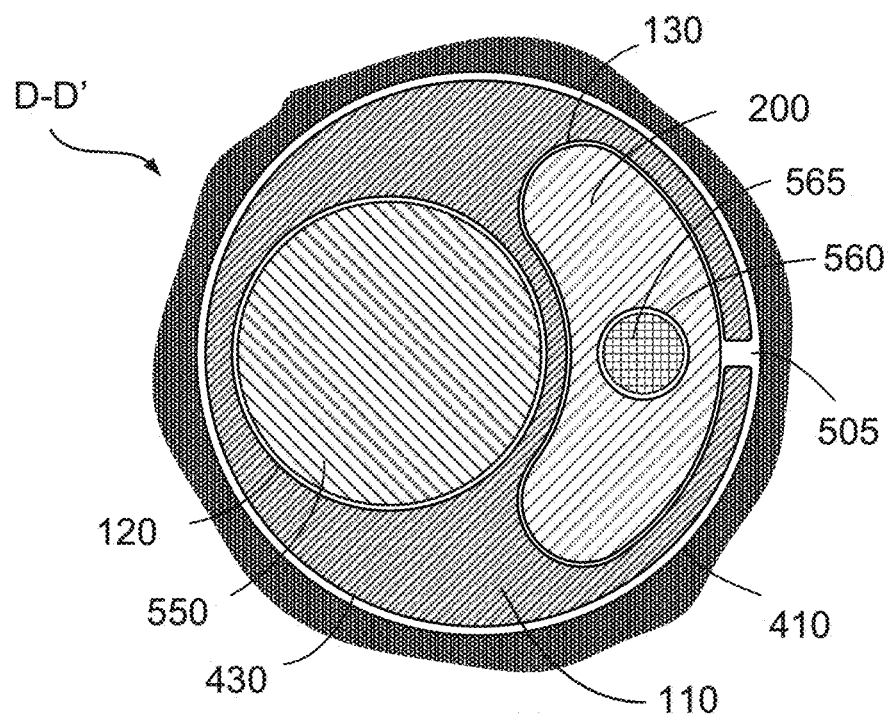
FIG. 5B shows a transverse cross section of the sheath assembly of FIG. 5A.

FIG. 5B illustrates a cross section of the sheath assembly 430 when located in the vessel 410 of the patient, taken along the cutline D-D' in FIG. 5A. The sheath assembly 430 comprises a sheath body 110 having a first lumen 120 and a second lumen 130. An aperture 505 is formed in the sheath body 110 and is in direct fluid communication with the second lumen 130. Retraction of the stylet 200 from the second lumen 130 allows fluid in the vessel 410 to flow through the sheath assembly 430. For the portion 432 of the sheath assembly 430 that is located within the arteriotomy 440, fluid is able to flow from the second lumen 130 through the aperture 505 and back into the vessel 410 thereby maintaining flow of fluid in the vessel 410. This is particularly alleviating for patients in vasospasm and the like. FIG. 5B also illustrates the passage of a medical device 550 in the first lumen 120. A stylet 200 is also positioned in the second lumen 130. Also shown in FIG. 5B is a central lumen 560 formed within the stylet 200, the central lumen 560 being occupied by a guidewire 565. In certain implementations an internal stylet could be inserted into the central lumen 560 instead of a guidewire. In further implementations, an internal stylet and a guidewire 565 could be used interchangeably in central lumen 560. In some implementations, the central lumen 560 is empty and terminates at the proximal end with an elastomer valve or plug.

Figure 5C:
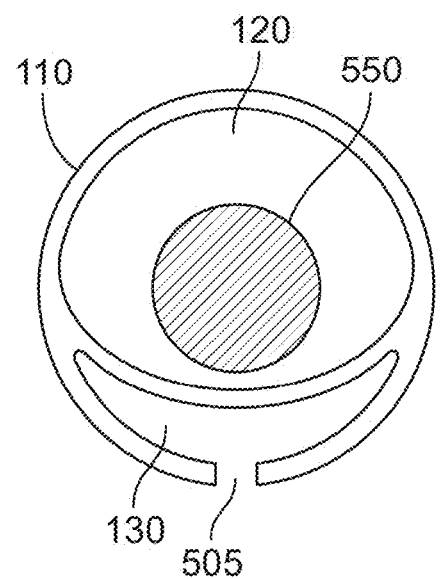
FIG. 5C shows an alternative transverse cross section of the sheath assembly of FIG. 5A.
Figure 5D:
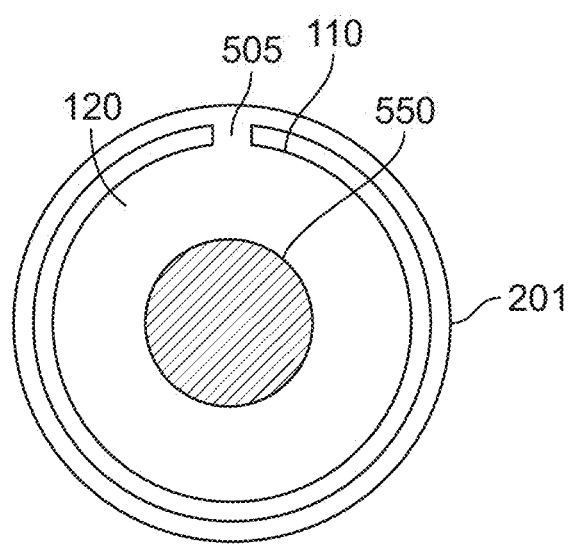
FIG. 5D shows an alternative transverse cross section of a sheath assembly similar to the sheath assembly of FIG. 5A.

FIGS. 5C-5D show geometries for the cross section of the sheath assembly 430 when located in the vessel of the patient, taken along the cutline D-D' in FIG. 5A. The sheath assembly 430 comprises a first lumen 120 and a second lumen 130. Medical device 550 passes through the first lumen 120. Second lumen 130 has an aperture 505 for receiving a stylet 200. As the stylet 200 is moved longitudinally respective to the sheath body 110, stylet 200 occludes aperture 505. When stylet 200 is removed, it exposes the aperture 505 such that blood can flow through the second lumen 130 and out of the sheath through aperture 505. Alternatively, rather than use a stylet 200 to selectively occlude or open apertures in the sheath body 110, an outer sheath or sleeve 201 is used. As shown in FIG. 5D, outer sheath or sleeve 201 surrounds sheath body 110, which has a first lumen 120 through which medical device 550 passes through. Sheath body 110 includes aperture 505, which can be occluded or uncovered through relative longitudinal motion of outer sheath or sleeve 201 relative to the sheath body 110. Outer sheath or sleeve 201 and sheath body 110 are concentric. A gap exists between outer sheath or sleeve 201 and sheath body 110. In an example, the gap has a width between about 0.1 cm and 0.5 cm. As discussed above in relation to FIG. 5A, apertures 505-509 are formed along the length of the sheath body 110. With the configuration of FIG. 5D, these apertures 505-509 terminate in the first lumen 120. The apertures 505-509 are formed along the length of the sheath body 110 such that they are located substantially along the bend of the sheath assembly 430 as it transitions from the insertion angle at the arteriotomy 440 to a position where the sheath lays axial with the vessel 410. When the sheath assembly 430 is positioned in the vessel 410, at least some of the apertures 505-509 formed in the sheath body 110 will be in direct fluid communication with the second lumen 130 so as to allow fluid flowing in the second lumen to exit the sheath body 110 and flow towards the end 414 of the vessel 410 as indicated by arrow C in FIG. 4. In some examples the outer sheath or sleeve 201 surrounds sheath body 110 and extends distal of the bend of the sheath assembly 430. The outer sheath or sleeve 201 may surround sheath body 110 and extend proximal of the bend of the sheath assembly 430. In one adaptation, the outer sheath or sleeve 201 is introduced into the body of the patient as part of the sheath assembly 430 and the outer sheath or sleeve 201 fully covers apertures 505-509 formed along the length of the sheath body 110. After insertion, and depending on observed or desired limb perfusion, by moving outer sheath or sleeve 201 the clinician or other caregiver selectively opens a number of apertures 505-509. When an aperture 505 is opened, i.e. the outer sheath or sleeve 201 has been slid in a proximal direction to no longer cover aperture 505, blood flows from a location upstream of the sheath assembly, through the distal end of the sheath assembly, through open aperture 505, and into the portion of the artery distal of the arteriotomy.

Figure 6:
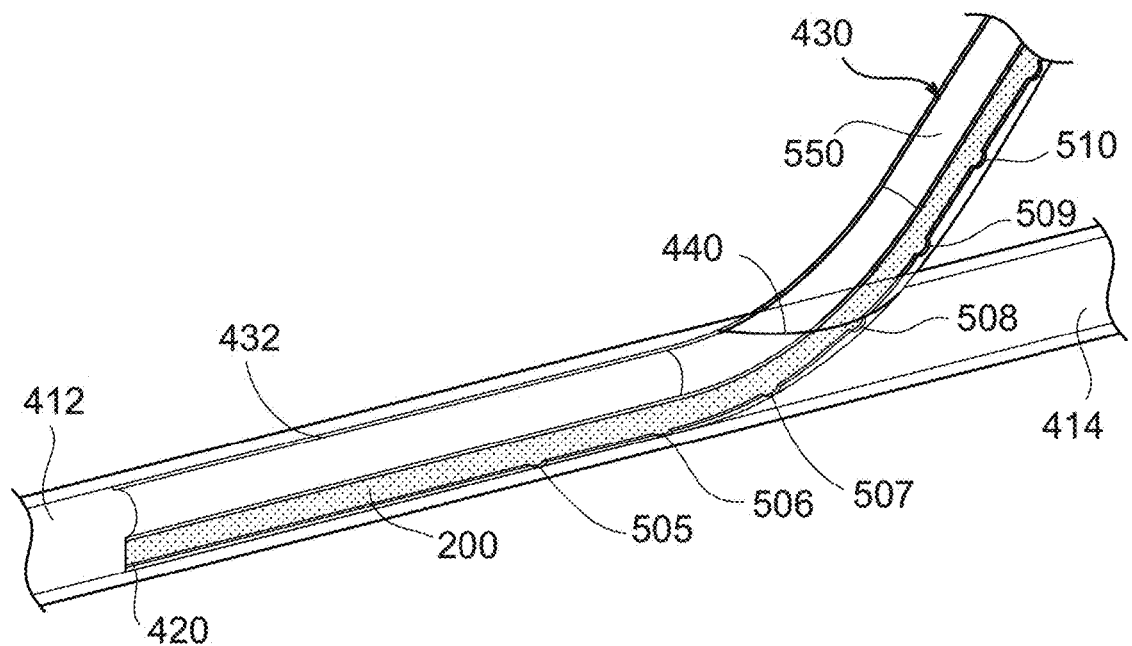
FIG. 6 shows an isometric view of the medical device inserted into the sheath assembly of FIG. 5B.

FIG. 6 illustrates a sheath assembly 430 of FIGS. 5A and 5B inserted into the arteriotomy 440 of a patient. When the sheath assembly 430 is inserted in position, the distal end 420 of the sheath assembly 430 is axially aligned with the vessel 410. With the sheath assembly 430 inserted as illustrated in FIG. 6, apertures 505-508 are located within the vessel 410 while apertures 509-510 are external to the vessel 410. Thus in the absence of a stylet in the second lumen 130, apertures 505-508 enable the second lumen 130 and the vessel 410 to be in fluid communication with each other. FIG. 6 also shows a medical device 550 inserted in the first lumen 120 and a stylet 200 inserted in the second lumen 130. Here the stylet 200 is fully inserted in the second lumen 130. The stylet 200 plugs the second lumen 130 to prevent fluid from entering the distal end 420 of the lumen 130, thereby preventing fluid communication from the second lumen 130 to the outside of the sheath assembly 430 through apertures 505-508. This configuration represents the insertion configuration where no fluid bypass is desired.

Figure 7:
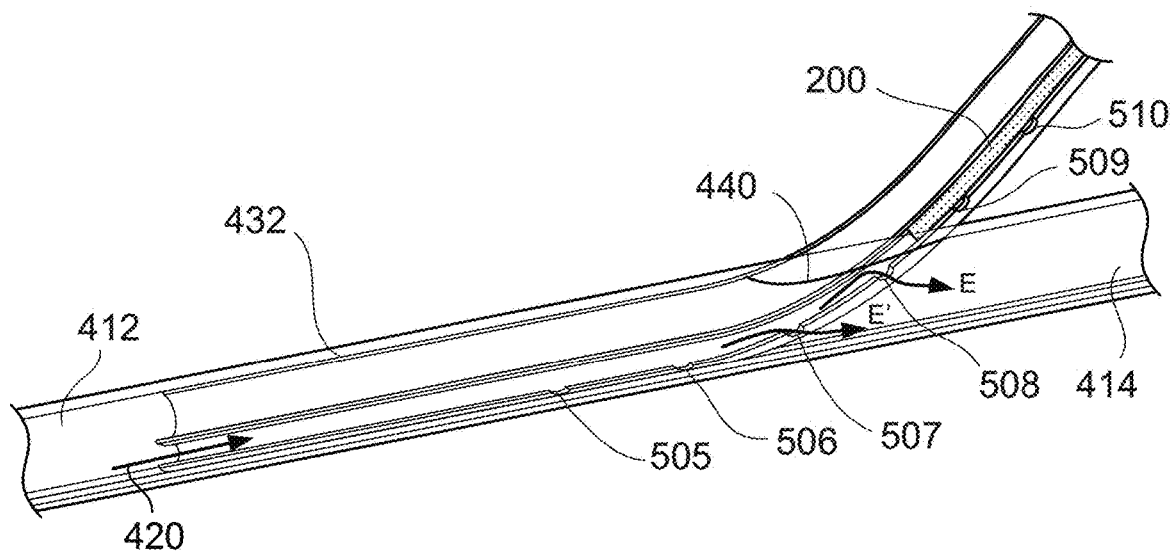
FIG. 7 shows an isometric view of the medical device inserted into the loaded sheath of FIG. 6 with the stylet partially retracted.

FIG. 7 illustrates the sheath assembly 430 as depicted in FIG. 6, with the stylet 200 partially retracted from the second lumen 130 when fluid bypass through the sheath assembly 430 is required. The stylet 200 is partially retracted in that apertures 505-508 formed in the sheath body 110 (as depicted in FIG. 7) are uncovered while the remaining apertures 509-510 in the sheath body 110 remain covered by the stylet 200. The retraction of the stylet 200 past at least one of the apertures allows for fluid to flow in the second lumen 130 from the distal end 420 of the sheath assembly 430 (the distal end 420 of the sheath assembly 430 residing in the distal portion 412 of the of the vessel 410) through the uncovered apertures 505-508 to the end 414 of the vessel 410. Arrows E and E' in FIG. 7 indicate such fluid flow. This configuration represents the state in which blood perfusion to the limb is enabled with the sheath completely filling the vessel 410 (e.g. patients in vasospasm). The stylet 200 is shown to expose apertures 505-508 within the vessel 410 to allow for fluid flow, but does not expose apertures 509-510 outside of the vessel 410 so as to prevent fluid flow into the subcutaneous tissue 405 and insertion track. Determination of the correct position of the stylet 200 relative to the sheath assembly 430 which allows flow in the vessel 410 while preventing fluid to enter the subcutaneous tissue and insertion track is critical. A method of determining this position will be discussed in the sections that follow.

In any of the foregoing implementations, each aperture should provide a cross sectional area that is similar to the cross sectional area of the second lumen 130 since only one aperture is opened at a time in the vicinity of the arteriotomy 440 when the stylet 200 is retracted. This allows for optimal distal perfusion without causing a build-up of pressure within the vessel 410. Additionally while any shape of aperture can be used, the shape used in the foregoing implementations is selected such that the stylet 200 can be safely advanced across the bend in the vicinity of the arteriotomy 440 without the risk of the stylet 200 exiting any one of the apertures.

While a limited number of apertures is illustrated in FIGS. 5A, 6 and 7, any number of apertures can be formed along the length of the sheath body 110 to connect the external surface 118 of the sheath body 110 with the second lumen 130. In some implementations, multiple apertures at a given length of the sheath body 110 are formed to minimize the risk of one aperture being occluded during use. In other implementations, a continuous channel along the length of the sheath body 110 is used instead of multiple discrete apertures. In further implementations, the apertures are arranged according to a distribution pattern along the length of the sheath body 110 to minimize the risk of blockage by an obstruction in the vessel 410. Such distribution patters include, but are not limited to, linear, logarithmic, graded, for example.

Figure 8A:
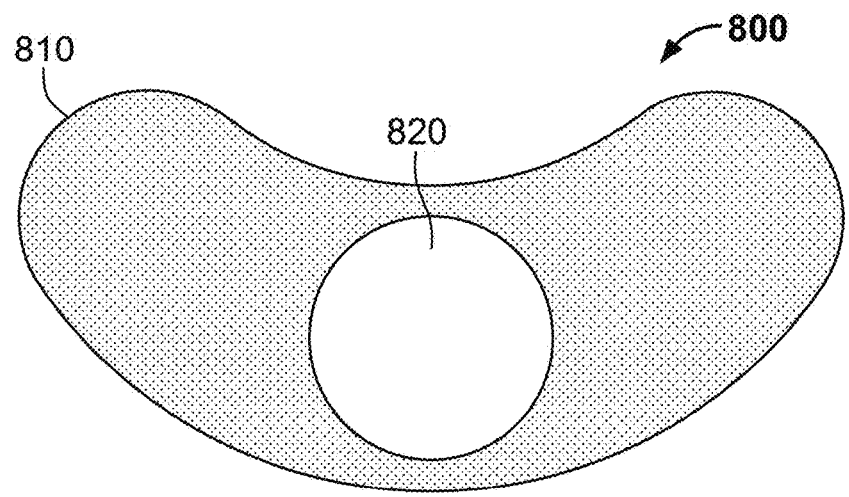
FIG. 8A shows a transverse cross section of a stylet similar to that of FIG. 2 with a lumen running through the longitudinal length of the stylet body.
Figure 8B:
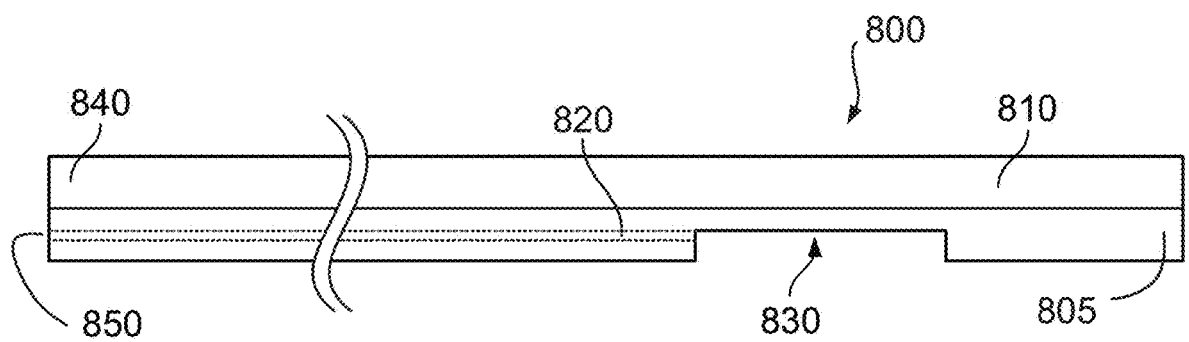
FIG. 8B shows a side view of the stylet of FIG. 8A with a skive formed at a distal end of the stylet body.
Figure 8C:
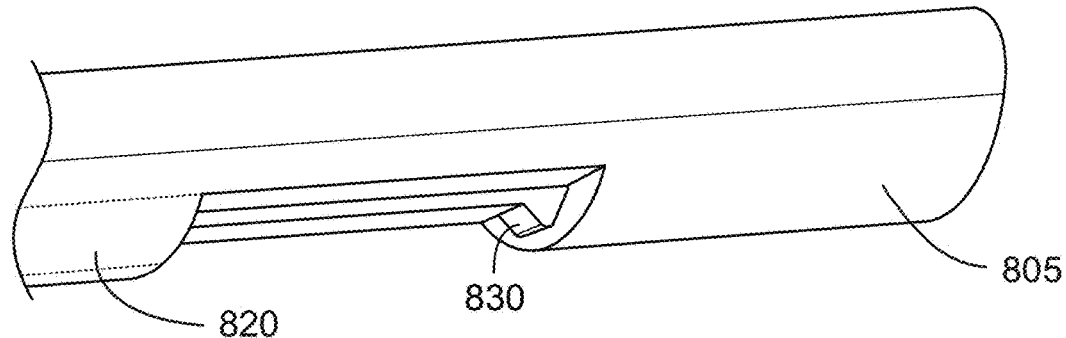
FIG. 8C shows an isometric view of the distal end of the stylet of FIG. 8B.

FIG. 8A illustrates a cross section of a stylet 800 according to an implementation of the present disclosure. Stylet 800 is similar to stylet 200 in FIG. 2, however in FIG. 8A the stylet body 810 has a central lumen 820 running through a portion of the length of the stylet 800. Central lumen 820 is similar to central lumen 560 shown in FIG. 5B. A side view of the stylet 800 is shown in FIG. 8B showing a skive 830 formed in the distal end 805 of the stylet 800. FIG. 8B also shows that a fluid passage within the stylet 800 that runs from the skive 830 through the central lumen 820 and terminates at the proximal end 840 of the stylet 800. The central lumen 820 terminates at the proximal end 840 of the stylet 800 at opening 850. The distal end 805 of the stylet 800 is plugged. In certain embodiments, the distal end 805 may be open to allow for the passage of a guidewire, for example. The skive 830 provides fluid communication from outside the stylet 800 in proximity to the skive 830 to the second lumen 130 when the stylet 800 is used in conjunction with the sheath assembly 430. FIG. 8C shows an isometric view of the skive 830 in the distal end 805 of the stylet 800. As can be seen from FIGS. 8A to 8C, the central lumen 820 and the skive 830 form a passage for the flow of fluid from the skive 830 to the proximal end (not shown) of the stylet 800. This passage 800 terminates at the distal end 805 of the stylet 800 as the central lumen 820 does not extend beyond the skive 830 in the implementation depicted in FIGS. 8B and 8C. In other implementations, markings are formed on the stylet body 810 towards the proximal end 840 of the stylet 800 to indicate the position of the stylet with respect to the distal tip 420 of the sheath assembly 430 or with respect to the apertures 505-510 formed in the sheath body 110. This allows for the position of the arteriotomy relative to the stylet to be easily determined.

In some implementations, the proximal end 425 of the sheath assembly 430 may be coupled to a hub, as are known in the field. The hub has an internal conduit that is in fluid communication with the first and second lumens 120, 130 of the sheath assembly 430 when the hub is coupled to the proximal end 425 of the sheath assembly 430. In other implementations, the first lumen 120 may be coupled to a first hub and the second lumen may be coupled to a second hub. In this configuration a medical device 550 is introduced into the sheath assembly 430 through the first hub, and a stylet 800 is inserted into the sheath assembly through the second hub. In some implementations the first hub and the second hub integrate with each other. In any of the foregoing implementations, the hub is provided with structures such as, but not limited to, suture holes or wings that facilitate attachment to the patient.

In some implementations, the insertion and extraction of the stylet 800 to selectively open and close the second lumen 130 is achieved with the use of a ratcheting mechanism attached to the proximal end 425 of the sheath assembly 430. Such a ratcheting mechanism ensures that the movement of the stylet 800 towards the proximal end 425 of the sheath assembly 430 is controlled in standard increments.

Use of the sheath assembly 430 as described in relation to FIGS. 4, 5A, 6 and 7 for selective fluid bypass will now be described in with respect to FIGS. 9A and 9B. A physician using the sheath assembly 430 with the stylet 800 will be able to determine the precise positioning of the stylet 800 relative to the sheath assembly 430 and arteriotomy 440 to enable fluid bypass through the second lumen 130. This is indicated by the presence of fluid at the opening 850 at the proximal end 840 of the stylet 800. In FIGS. 9A and 9B the sheath assembly 430 is shown straightened for the purposes of illustration. Accordingly, the arteriotomy 440 is shown as a slanted line such that the sheath assembly 430 to the left of the line 440 resides in the target vessel 410 and the sheath assembly 430 to the right of the line 440 resides outside of the target vessel 410.

FIG. 9A illustrates a cross section of the sheath assembly 430 in the target vessel 410 (not shown) in a first configuration. FIG. 9A shows the first lumen 120 and the second lumen 130 of the sheath, and apertures 932-935 in the sheath body which are in fluid communication with the second lumen 130. In FIG. 9A the stylet 800 is partially retracted where apertures 932-934 are located within the vessel 410 (located to the left of the arteriotomy 440) and aperture 935 is external to the vessel 410 (located to the right of the arteriotomy 440).

The skive 830 of stylet 800 is in fluid communication with the central lumen 820. The length of the skive 830 is less than the distance between the apertures 932-935 of the sheath assembly 430. FIG. 9A shows the stylet 800 positioned so that blood from the vessel 410 and entering through the distal tip 420 of the sheath assembly 430 can exit the first and second apertures 932-933 with the distal tip 805 of the stylet 800 blocking blood flow through the rest of the second lumen 130 of the sheath assembly 430. As mentioned with respect to FIGS. 8A-8C, the stylet 800 has a plugged distal tip 805 preventing fluid communication from the distal end 805 of the stylet 800 to the skive 830. Thus any blood flowing from the distal end 420 of the second lumen 130 in the sheath assembly 430 has to exit the second lumen 130 via apertures 932-933 and re-enter the stylet 800 via skive 830 to flow into the central lumen 820.

The third aperture 934, located in the target vessel 410, resides within the length of the skive 830. This provides fluid communication form the vessel 410 through the aperture 435, into the skived area 830 (see arrow F), and down the central lumen 820 of the stylet 800. The pressurized blood flow of the vessel 410 would cause visible and pulsatile bleeding to exit the proximal end 840 of the stylet 800. This blood flow would be visible at opening 850 of the central lumen 820 at the proximal end 840 of the stylet 800. The position of the skive 830 also terminates before the fourth aperture 935 with the body 810 of the stylet 800 blocking any fluid communication through aperture 935. In this configuration the presence of blood flow on the proximal end 840 of the stylet 800 would indicate that there is at least one aperture proximal to the distal end 805 of the stylet 800 within the vessel 410, and that the stylet 800 can be retracted further.

FIG. 9B illustrates a cross section of the sheath assembly 430 in the target vessel 410 in a second configuration following the first configuration as described above. In the second configuration the stylet 800 is positioned in the sheath assembly 430 such that blood entering through the distal tip 420 of the sheath assembly 430 can exit the first, second and third apertures 932-934 with the distal end 805 of the stylet 800 blocking flow through the rest of the second lumen 130 of the sheath assembly 430. The fourth aperture 935, located outside of the vessel 410 (to the right of the arteriotomy 440), resides within the length of the skive 830. This prohibits fluid communication from the vessel 410, through the second lumen 130, into the skived area 830, and down the central lumen 820 of the stylet 800. The pressurized blood flow of the vessel 410 no longer causes pulsatile bleeding at the exit 850 of the proximal end 840 of the stylet 800. In this configuration the lack of blood flow at the proximal end 840 of the stylet 800 would indicate that there are no apertures proximal to the distal end 805 of the stylet 800 within the target vessel 410.

The transition from the first configuration (visible blood flow out of the exit 850 of the proximal end 840 of the stylet 800) in FIG. 9A to the second configuration (no blood flow out of the exit 850 of the proximal end 840 of the stylet 800) in FIG. 9B would indicate that the stylet 800 is positioned in the ideal location with respect to the sheath assembly 430 and the arteriotomy 440 for blood bypass through the sheath assembly 430.

Figure 10:
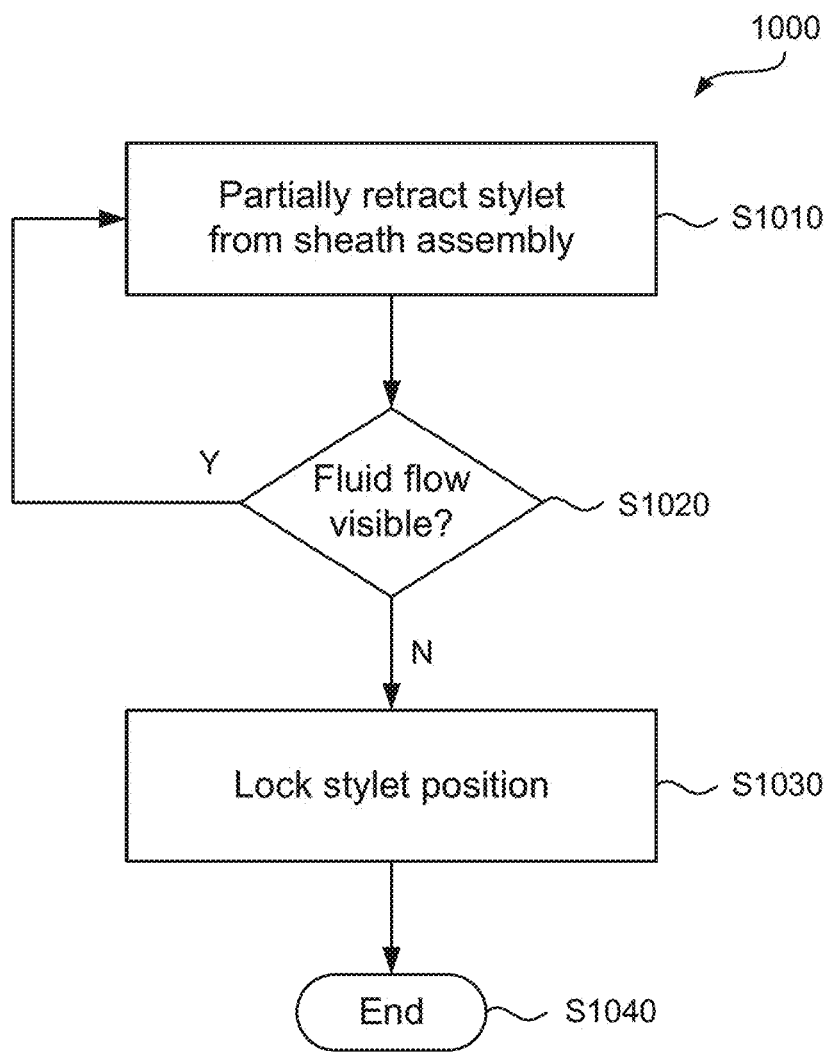
FIG. 10 shows an illustrative method for adjusting the position of the stylet relative to the sheath for fluid bypass through the second lumen of the sheath.

FIG. 10 shows an illustrative method 1000 of using the persistent perfusion sheath assembly 430. Such an assembly would comprise a sheath body 110 with a first lumen 120 and a second lumen 130, where the first lumen 120 provides a passageway for a medical device the second lumen 130 is loaded with a stylet 800 for selectively opening and closing the second lumen for blood bypass through the sheath assembly 430. The illustrative method 1000 may be performed using the persistent perfusion sheath assembly 430 or any other suitable sheath assembly tool. The method 1000 starts at step S1010 when the sheath assembly 430 is positioned in a target blood vessel, with a physician is looking to create blood bypass through the sheath (e.g. in a patient experiencing vasospasm). In step S1010 the physician partially retracts a stylet 800 from the sheath assembly 430. This is done by pulling the distal end 805 of the stylet 800 towards the distal end 420 of the sheath assembly 430 while ensuring that the sheath assembly 430 remains in position within the arteriotomy of the patient.

In step S1020 the physician stops retracting the stylet 800 and checks the opening 850 at the distal end 805 of the stylet 800 for visible and pulsatile bleeding. If there are signs of flowing blood at the opening 850, i.e. a 'Yes' in the determining step S1020, the physician repeats S1010 and continues to partially retract the stylet 800 from the sheath assembly 430. This is the situation as described in relation to FIG. 9A, the first configuration. If the blood flow from the opening 850 at the distal end 805 of the stylet 800 stops, i.e. a 'No' in the determining step S1020 (as in the second configuration as depicted in FIG. 9B), the method proceeds to step S1030 where the physician secures or locks the position of the partially retracted stylet 800 relative to the sheath assembly 430. The fluid bypass is then achieved and the method ends at step S1040.

In view of the foregoing, the person of ordinary skill will appreciate that the present disclosure provides a means to allow the flow of blood in a constricted blood vessel while a medical procedure is underway. This avoids the need to adopt other surgical methods (such as a fem-to-fem bypass) which would increase complexity and cost of the medical procedure.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system percutaneous heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

Figure 11:
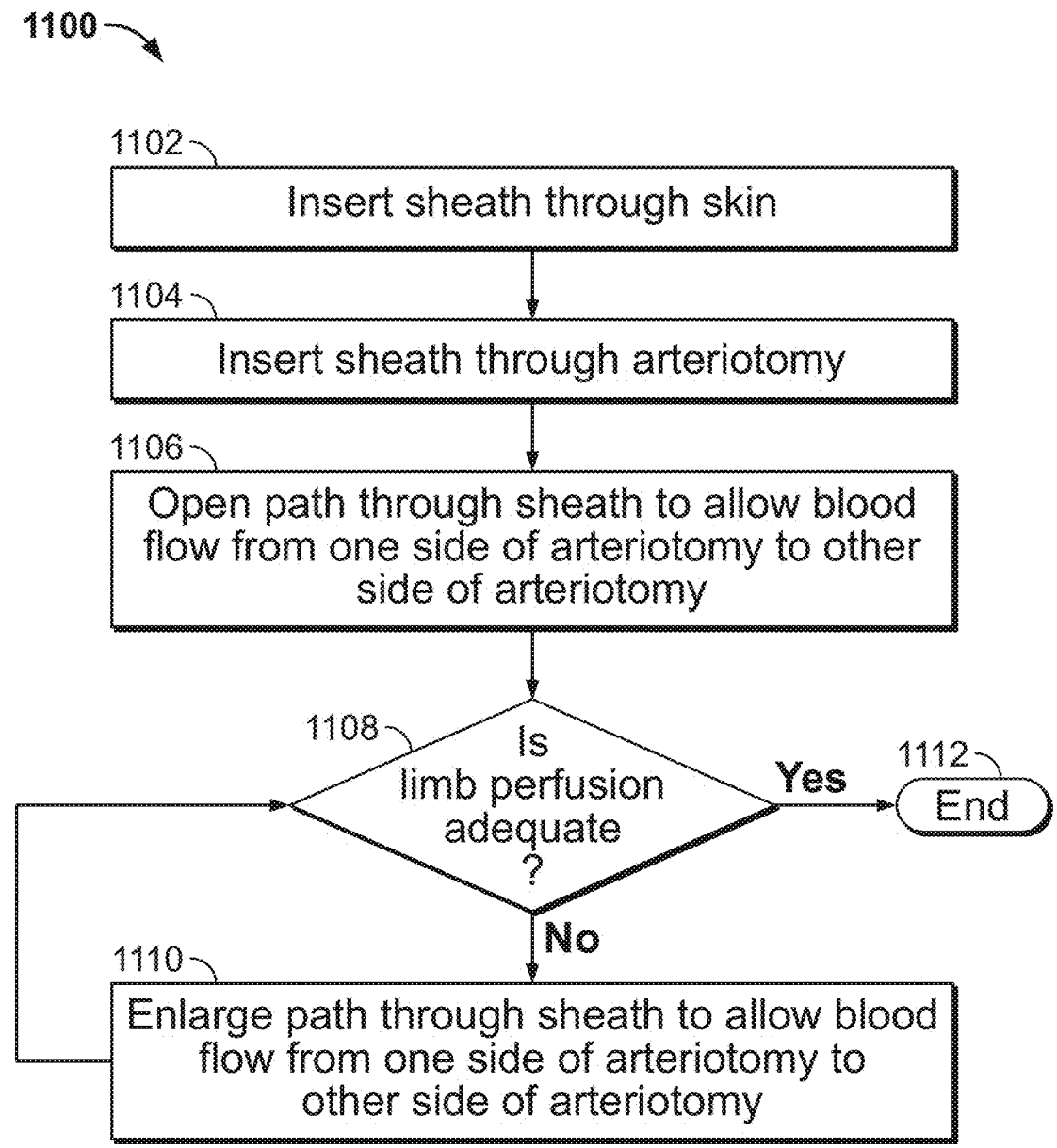
FIG. 11 shows an illustrative method for providing adequate limb perfusion while using a sheath assembly.
Figure 13:
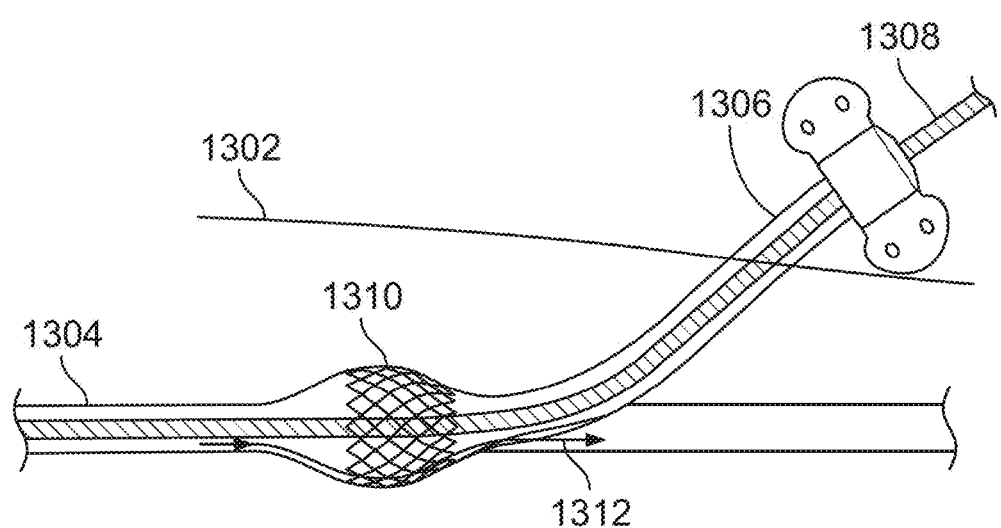
FIG. 13 shows an illustrative view of a sheath with a distal expandable portion according to an implementation of the present disclosure.
Figure 14:
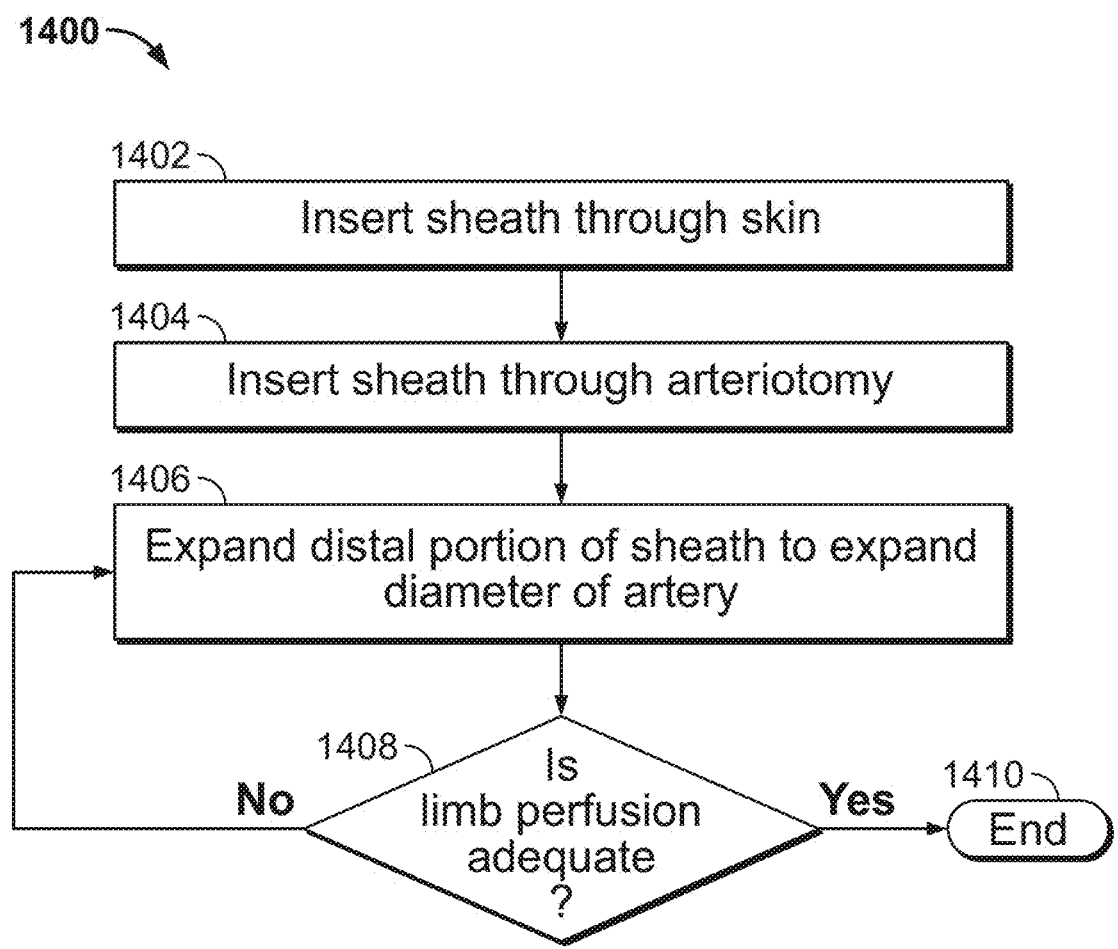
FIG. 14 shows an illustrative method for providing adequate limb perfusion using the sheath of FIG. 13.

FIG. 11 shows an illustrative method 1100 for providing adequate limb perfusion while using a sheath assembly. In an initial procedure, a clinician or other caregiver creates a puncture through the skin of a patient and percutaneously inserts a sheath through the puncture site and into the artery of the patient through an arteriotomy (steps 1102, 1104). Additional steps may be performed by the clinician or caregiver between the puncture and the arteriotomy on one hand, and insertion of the sheath through the puncture and the arteriotomy on the other hand. For example, the clinician or other caregiver may use a guidewire, and successive dilators to gradually enlarge both the puncture and the arteriotomy sufficiently to accommodate the sheath, which can be an introducer sheath or a repositioning sheath. The sheath is advanced until its distal end is positioned within the artery and the proximal end of the sheath is positioned outside the patient. After deploying the sheath, the physician opens a path through the sheath to allow blood to flow from one side of the sheath to the other—i.e., so the blood flows past the sheath (e.g., around or through the sheath) from a location upstream of the arteriotomy and reaches the downstream vasculature of the patient, downstream of the arteriotomy. In one example, the path allows blood to flow from the portion of the artery upstream of the arteriotomy to the portion of the artery downstream of the arteriotomy (and downstream of the sheath), thereby achieving limb perfusion. Opening a path through the sheath to allow blood to flow past the sheath within the artery can be done for example by using any of the systems described herein in relation to FIGS. 1-9 and FIG. 12 (selectively opening apertures in the sheath by retracting a device occluding the apertures in the sheath); FIGS. 13-14 (expanding a distal portion of the sheath to expand the diameter of the artery), FIGS. 15-16 (connecting a blood flow channel through the sheath to a second sheath inserted in the artery downstream of the arteriotomy for the first sheath); or FIGS. 17-19 (inflating a balloon attached to an outer surface of the sheath, thereby expanding the artery diameter).

The clinician or other caregiver checks whether limb perfusion is adequate (e.g. step 1108). For example, a physician can check periodically the capillary refill of a limb of the patient located distal of the arteriotomy. If the clinician or other caregiver determines that limb perfusion is adequate (step 1108), no action is needed from the clinician or other caregiver to further open up a blood flow path (step 1112). If instead the clinician or other caregiver determines that limb perfusion is inadequate (step 1108), the clinician or other caregiver enlarges the path through the sheath (step 1110) to allow more blood to flow from the portion of the artery upstream of the arteriotomy to the portion of the artery downstream of the arteriotomy, to improve the limb perfusion. Similar to opening an initial path through the sheath to allow blood to flow from the upstream side of the sheath to the downstream side, widening or further opening the initial path can similarly be done by using any of the systems described herein in relation to FIGS. 1-9 and FIG. 12 (further retracting a device occluding the apertures in the sheath to open more apertures); FIGS. 13-14 (further expanding a distal portion of the sheath to further expand the diameter of the artery), FIGS. 15-16 (adapting the connection between the blood flow channel through the sheath and the second sheath inserted in the artery distal of the arteriotomy for the first sheath to increase flow rate to the second sheath); or FIGS. 17-19 (further inflating a balloon attached to an outer surface of the sheath, to further expand the artery diameter). The clinician or other caregiver again checks again whether limb perfusion is adequate (step 1108). At least one benefit of method 1100 are the ability to address instances where blood flow from upstream of the arteriotomy to downstream of the arteriotomy is insufficient to maintain adequate limb perfusion. At least an additional benefit of method 1100 is the ability to adjust the amount of blood flowing past the sheath (e.g., around or through the sheath) from a location upstream of the arteriotomy and reaching the downstream vasculature of the patient, downstream of the arteriotomy, based on the particular circumstances of a patient and a procedure.

Figure 12:
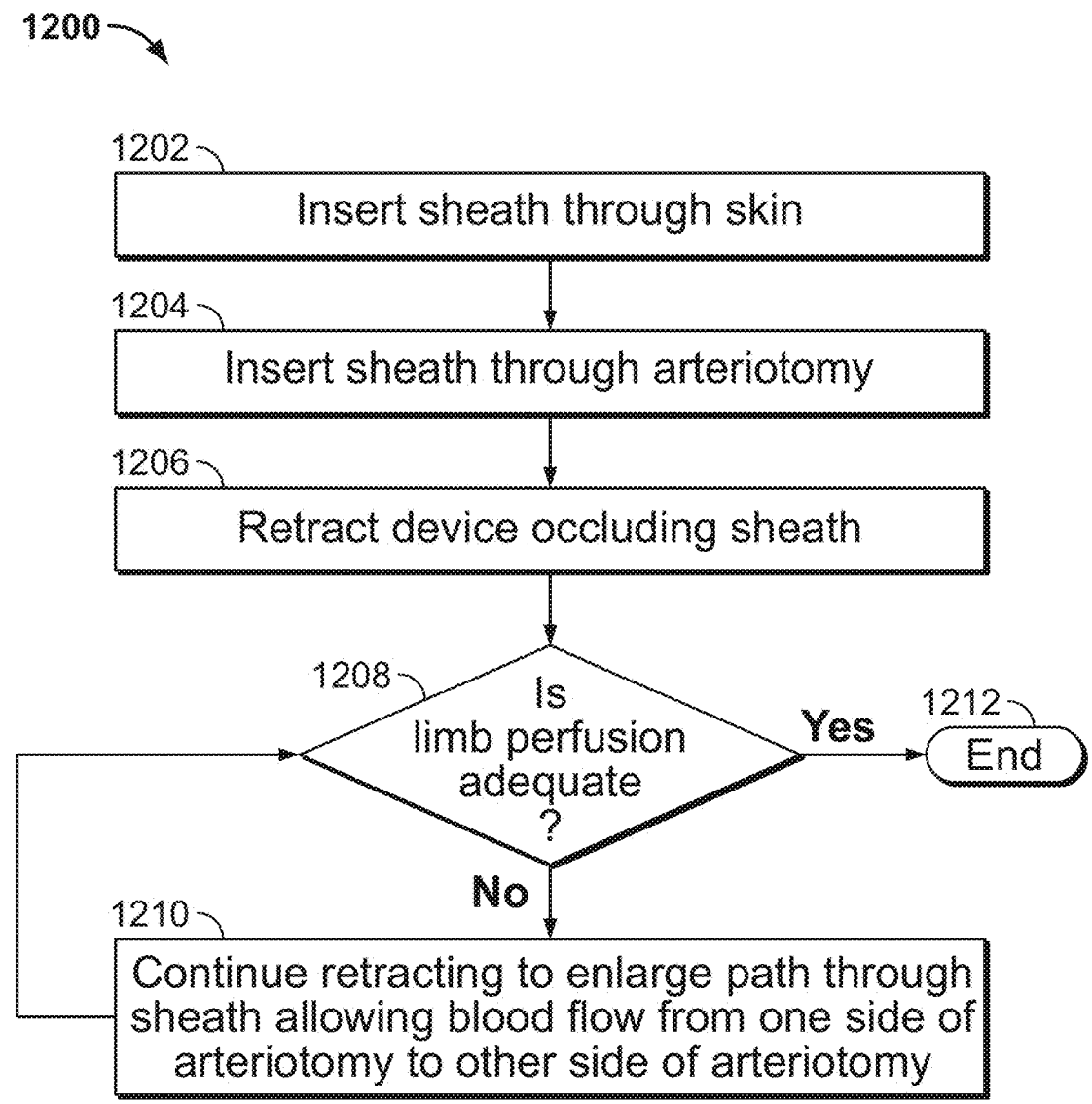
FIG. 12 shows an illustrative method for providing adequate limb perfusion while using a sheath assembly by retracting a device occluding the sheath.

FIG. 12 shows an illustrative method 1200 for providing limb perfusion using a sheath assembly by retracting a device occluding the sheath, thereby facilitating blood flow downstream of the sheath. In an initial procedure, a clinician or other caregiver creates a puncture through the skin of a patient and percutaneously inserts a sheath through the puncture site and into the artery of the patient through an arteriotomy (steps 1202, 1204). Additional steps may be performed by the clinician or caregiver between the puncture and the arteriotomy on one hand, and insertion of the sheath through the puncture and the arteriotomy on the other hand. The sheath is advanced until its distal end is positioned within the artery and the proximal end of the sheath is positioned outside the patient. At this point, the sheath can be used to introduce a medical device through the sheath and into the artery of the patient. The medical device is operated. During insertion or operation of the medical device, the clinician or caregiver may initially check whether limb perfusion is adequate. If the clinician or caregiver makes an initial determination that limb perfusion is inadequate, the clinician or other caregiver retracts a device occluding the sheath (step 1206), thereby opening a path through the sheath to allow blood to flow from upstream of the arteriotomy to downstream of the arteriotomy. In one example, the clinician or caregiver may retract a device occluding the sheath by a first amount by default, regardless of the level of limb perfusion observed initially. For example, the sheath can have apertures, slots or both along its length, as described above in relation to FIGS. 1-9. In one example, the occluding device is a stylet selectively movable through a lumen of the sheath, as described above in relation to FIGS. 1-9. In another example, the occluding device is an outer sheath or sleeve surrounding the sheath, as described above in relation at least to FIG. 5D. The path opened by retracting the occluding device allows blood to flow from the portion of the artery upstream of the arteriotomy to the portion of the artery downstream of the arteriotomy, providing limb perfusion.

Periodically, after the initial check, the clinician or other caregiver checks whether the limb perfusion is adequate (step 1208). For example, a physician can check the capillary refill of a patient's limb at a position located distal of the arteriotomy. If the clinician or other caregiver determines that limb perfusion is adequate (step 1208), no action is needed from the clinician or other caregiver to further open up a blood flow path (step 1212.) If instead the clinician or other caregiver determines that limb perfusion is inadequate (step 1208), the clinician or other caregiver enlarges the path through the sheath (step 1210) to allow more blood to flow from the portion of the artery upstream of the arteriotomy to the portion of the artery downstream of the arteriotomy, to improve the limb perfusion. For example, if using a stylet to selectively occlude or uncover apertures in the sheath, the clinician or other caregiver would further retract the stylet, i.e. retract the stylet by a greater amount, to uncover more apertures in the sheath, thereby increasing the cross-sectional area of the open blood flow path. In another example, if using an outer sleeve to selective occlude or uncover apertures in the sheath, the clinician or other caregiver would further retract the outer sleeve to uncover more apertures in the sheath, thereby increasing the cross-sectional area of the open blood flow path. Similar to the advantages of method 1100, at least some of the advantages of method 1200 are the ability to adjust the amount of blood flow to be let through from an upstream side of the arteriotomy to a downstream side of the arteriotomy based on the particular circumstances of a patient and a procedure.

In one example, steps 1202-1206 of method 1200 can be informed by an existing arteriotomy reference point. Without an existing arteriotomy reference point, the clinician or other caregiver can adjust an amount by which the device occluding the sheath is withdrawn by knowing a geometry of the device occluding the sheath and by monitoring blood flow at the access site, as described in relation to FIGS. 9A-B. With an existing arteriotomy datum, the clinician or other caregiver can rely on an established arteriotomy reference point established prior to inserting the sheath or the device occluding the sheath, and indicating that the arteriotomy is at a known and fixed distance from the skin of the patient. Accordingly, the clinician or other caregiver can compare the arteriotomy datum to a length of the device occluding the sheath to determine how to move the device occluding the sheath relative to the sheath to obtain the desired flow. An exemplary method for establishing an arteriotomy reference point is described below in reference to FIG. 21.

FIG. 13 shows an illustrative view of a sheath with a distal expandable portion according to an implementation of the present disclosure. The sheath 1306 is introduced through the skin 1302 and into an artery 1304 of a patient. For example sheath 1306 is introduced using steps similar to steps 1102-1104 of method 1100. A catheter 1308 runs through the sheath and into the artery. The sheath 1306 comprises a distal expandable portion 1310. In the example shown in FIG. 13 the distal expandable portion 1310 is a mesh. The clinician or other caregiver expands the distal expandable portion 1310 in situ to open a path through the sheath 1306 to allow blood to flow from upstream of the arteriotomy to downstream of the arteriotomy (see e.g. step 1106 of method 1100 in FIG. 11). As shown in the example of FIG. 13, when the distal expandable portion 1310 is expanded, the distal expandable portion 1310 creates a path 1312 for blood to flow from a location in the artery upstream of the arteriotomy, through the porous distal expandable portion 1310 of the sheath, and into a location in the artery downstream of the arteriotomy.

When expanded, the distal expandable portion 1310 has a varying cross-section along its length. For example, when expanded, a cross section of the upstream end of distal expandable portion 1310 is larger than a cross section of the downstream end of distal expandable portion 1310. In an example the cross-section of the distal expandable portion is circular along the length of the distal expandable portion. In one example, the distal expandable portion is a surface of revolution formed by an S-shaped curve. In one example, the distal expandable portion is made of a porous material, for example polytetrafluoroethylene (PTFE). In another example, the distal expandable portion is made of a mesh with openings or windows between mesh elements. In some examples the distal expandable portion 1310 can be woven or laser cut. In another example, the distal expandable portion 1310 can be a stent, attached to a distal end of the sheath 1306. In one example, the distal expandable portion 1310 can be biased open to have a rest state with a larger diameter, and can be expanded by withdrawing a portion of the sheath 1306 constraining the distal expandable portion 1310. Alternatively, in another example the distal expandable portion 1310 is biased closed, expanded in situ using a balloon, and held in its expanded configuration by a mechanism, for example by friction between fibers of the expandable end portion 1310, or a mechanical locking mechanism. In other examples, alternative expansion mechanisms besides a balloon are used, including any expansion mechanisms used for stents.

An expanded shape of the distal expandable portion 1310 is configured to open the path through the sheath 1306 to allow blood to flow from upstream of the arteriotomy to downstream of the arteriotomy. For example, the shape of the distal expandable portion can be an S-shape with a first bend and a second bend. The respective curvatures of the first bend and the second bend, a slope of the segment between the first and second bends, or a combination of curvatures and slopes is configured to expand a diameter of the vessel upstream of the arteriotomy over a relatively small longitudinal distance. In some adaptations, a slope of the segment between the first and second bends is between about 20-80 degrees, between about 30 and 60 degrees, or about 40 or 50 degrees.

The length of the distal expandable portion of the sheath relative to a length of the sheath can vary. In one example, the length of the distal expandable portion of the sheath is fixed prior to insertion. In one example where the length of the expandable portion of the sheath is fixed prior to insertion, the length of the distal expandable portion of the sheath is selected to be less than half of the length of the sheath. In another example, where the length of the expandable portion of the sheath is fixed prior to insertion, the length of the distal expandable portion of the sheath is selected to be less than a quarter of the length of the sheath. In another example, the length of the distal expandable portion of the sheath changes in situ. For example by selectively unsheathing only a portion of the distal expandable portion of the sheath, a clinician or other caregiver may select a length of the distal expandable portion of the sheath best adapted to a geometry of the patient.

FIG. 14 shows an illustrative method 1400 for providing adequate limb perfusion using the sheath of FIG. 13. In an initial procedure, a clinician or other caregiver creates a puncture through the skin of a patient and percutaneously inserts a sheath through the puncture site and into the artery of the patient through an arteriotomy (steps 1402, 1404). Additional steps may be performed by the clinician or other caregiver between the puncture and the arteriotomy on one hand, and insertion of the sheath through the puncture and the arteriotomy on the other hand. The sheath is advanced until its distal end is positioned within the artery and the proximal end of the sheath is positioned outside the patient. In one example, after insertion of a medical device, and initial operation of the medical device, the clinician or other caregiver preemptively expands a distal portion of the sheath to enable blood to flow from upstream of the arteriotomy, through the distal expandable end of the sheath, and downstream of the arteriotomy. In another example, the clinician or other caregiver first checks whether limb perfusion is adequate (step 1408). As discussed above at least in relation to FIG. 13, expansion of the distal expandable portion of the sheath can be done via balloon expansion, unsheathing of a biased open device, and/or any other suitable mechanism, including any expansion mechanisms used to deploy stents. As a result, the expandable distal portion of the sheath has an expanded diameter which is greater than a proximal portion of the sheath, and which forces expansion of the artery. After checking whether the limb perfusion is adequate, if the clinician or other caregiver determines that limb perfusion is adequate (step 1408), no action is needed from the clinician or other caregiver to further open up a blood flow path (step 1410). If instead the clinician or other caregiver determines that limb perfusion is inadequate (step 1408), the clinician or other caregiver further adjusts or expands (step 1406) the distal expandable portion of the sheath to expand the diameter of the artery further to increase a size of a flow path for blood to flow from upstream of the arteriotomy to downstream of the arteriotomy, and improve distal perfusion. A physician can check periodically the capillary refill of a limb of the patient located distal of the arteriotomy.

In one example, if the clinician or other caregiver is using a balloon to expand the distal expandable portion, the clinician or other caregiver further inflates the balloon to further increase the artery diameter. In another example, the clinician or other caregiver expands a longer segment of the distal expandable portion of the sheath to increase the blood flow past the sheath (e.g., around or through the sheath) from a location upstream of the arteriotomy and to the downstream vasculature of the patient, downstream of the arteriotomy. In another example, the clinician or other caregiver selectively adjusts the expanded shape of the expandable distal portion to increase a size of the blood flow path, and increase the blood flow past the sheath (e.g., around or through the sheath) from a location upstream of the arteriotomy and to the downstream vasculature of the patient, downstream of the arteriotomy.

In one example, the clinician or other caregiver administers an anti-clotting agent during the course of the procedure. The anti-clotting agent prevents blood clotting in the pores or mesh openings of the distal expandable portion and occluding the distal expandable portion. The anti-clotting agent also minimizes the risk of clots being released into the bloodstream of the patient, causing a health risk. At least some advantages of the method 1400 and sheath illustrated in relation to FIGS. 13 and 14 are the ability to selectively expand or contract the distal expandable portion of the sheath, to adapt to varying patient geometries or arterial conditions.

Figure 15:
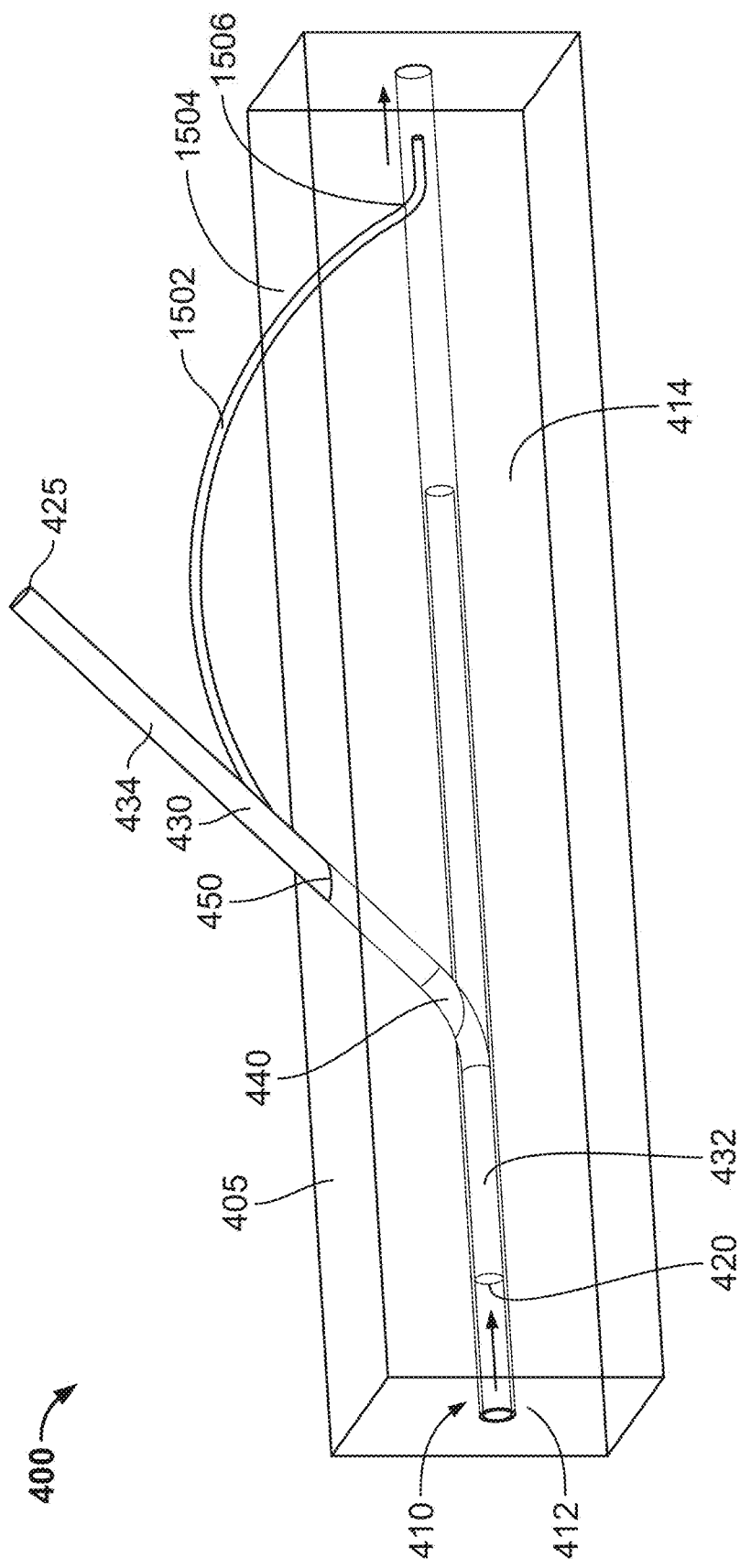
FIG. 15 shows an illustrative isometric view of a sheath assembly with two sheaths according to an implementation of the present disclosure.

FIG. 15 shows an illustrative isometric view of a sheath assembly with two sheaths according to an implementation of the present disclosure. FIG. 15 is similar to FIG. 4 of the present disclosure, but includes a second sheath 1502. Sheath 1502 is connected at a first end to the first sheath assembly 430, such that blood can flow from the sheath assembly 430 into sheath 1502. Sheath assembly 430 includes a lumen through which blood can flow from a distal end of sheath assembly 430 to more proximal location. For example, the lumen can be a lumen located within the sheath body, or a lumen formed between the sheath body and an outer sleeve, as described in relation to FIGS. 1-7. In another example, the lumen can be formed as a side-rigger channel along the sheath body. Blood flows from a location upstream of the arteriotomy through the sheath assembly 430 and into the sheath 1502. The second end of sheath 1502 perforates the skin of the patient at a location 1504 distal of the first skin puncture 450, and penetrates the artery of the patient at a second arteriotomy site 1506, downstream of the first arteriotomy. Accordingly blood can flow from a region upstream of the first arteriotomy through the sheath assembly and the second sheath into the second arteriotomy, and downstream of the second arteriotomy.

In one example, the length of the lumen is equal to a length of the sheath body. In another example, the length of the lumen is less than a length of the sheath body. The first end of the second sheath 1502 connects to the lumen anywhere along the length of the lumen, such that blood can flow from the lumen and into the first end of the second sheath 1502. In one example the first end of the second sheath 1502 connects to a proximal end of the lumen. In another example, the first end of the second sheath 1502 connects to the lumen anywhere along the length of the lumen. In one example, the proximal end of the lumen is outside of the skin of the patient, such that a clinician or other caregiver can easily connect the first end of the second sheath 1502 to the end of the lumen. In another example, the proximal end of the lumen is located below the skin of the patient, such that a clinician or other caregiver slides the first end of the second sheath 1502 into the first sheath to connect the first end of the second sheath 1502 to the proximal end lumen.

Figure 16:
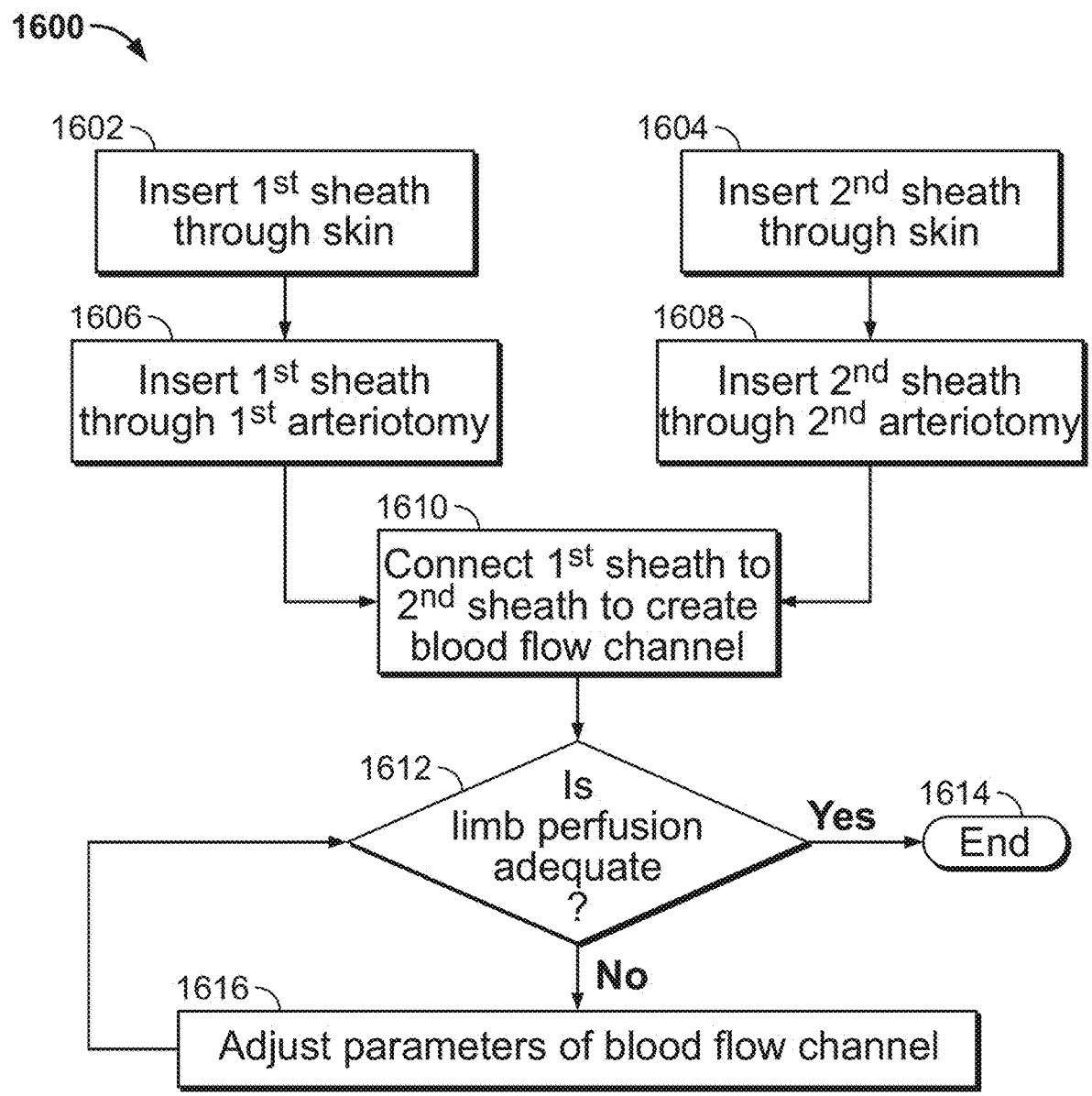
FIG. 16 shows an illustrative method for providing adequate limb perfusion using the sheath assembly of FIG. 15.

FIG. 16 shows an illustrative method for providing adequate limb perfusion using the sheath assembly of FIG. 15. In an initial procedure, a clinician or other caregiver creates a first puncture through the skin of a patient and percutaneously inserts a first sheath through the first puncture site and into the artery of the patient through an arteriotomy (steps 1602, 1606). As discussed above, e.g. in relation to FIG. 14, additional steps may be performed by the clinician or caregiver between the first puncture and the first arteriotomy on one hand, and insertion of the first sheath through the first puncture and the first arteriotomy on the other hand. The sheath is advanced until its distal end is positioned within the artery and the proximal end of the sheath is positioned outside the patient. In addition, a clinician or other caregiver creates a second puncture through the skin of a patient and percutaneously inserts a second sheath through the second puncture site and into the artery of the patient through an arteriotomy (steps 1604, 1608). The second sheath is similarly advanced until its distal end is positioned within the artery and the proximal end of the second sheath is positioned outside the patient. In one example, the insertion of the first and second sheaths can be done in parallel. In another example, the insertion of the first and second sheath can be done in succession.

After an initial check regarding whether limb perfusion is accurate, or as precautionary or default measure, the clinician or other caregiver then connects the first sheath to the second sheath to create a blood flow channel between a location upstream of the first arteriotomy and a location downstream of the second arteriotomy (step 1610). In one example, the clinician or other caregiver selects a longitudinal distance between the first arteriotomy and the second arteriotomy to be relatively small. A relatively small distance between first arteriotomy and second arteriotomy can be beneficial to minimize fluid losses and to minimize the risks of clots or sheath obstruction. For example, a distance between the first and second arteriotomy may be between about 5 cm and 20 cm, between about 10 cm and 15 cm, or about 12 cm to about 14 cm. The distance between the first and second arteriotomies may depend on the geometry of the patient and the characteristics of the procedure. For example, for a patient with veins which are harder to access, the distance between the first and second arteriotomies needs to be shorter than for a patient with easily accessible veins, closer to the skin surface. In another example, a patient may have a longer or shorter limb, and a greater or shorter distance respectively may be needed for the second sheath to access the artery at a suitable location downstream of the first arteriotomy. The clinician or other caregiver periodically checks whether limb perfusion distal of the first arteriotomy is adequate (step 1612). As discussed above in relation for example to FIG. 11, this can involve checking for capillary reflexes, and/or periodically checking skin color in the limb.

If limb perfusion is adequate, no action is needed from the clinician or other caregiver to further open up a blood flow path. Otherwise if limb perfusion is not adequate, the clinician or other caregiver adjusts the parameters of the blood flow channel between the first location upstream of the first arteriotomy and the second location downstream of the second arteriotomy (step 1616). In one example, the connection between the second sheath 1502 and the lumen through which blood passes from upstream of the arteriotomy to downstream of the arteriotomy (described in relation to FIG. 15) includes a valve. In this example, the clinician or other caregiver can adjust the amount of flow passing from the lumen to the second sheath 1502 by selectively opening, i.e. further opening the valve, to increase the flow of blood passing through the first sheath, into the second sheath, and into the artery downstream of the first arteriotomy. In another example, the clinician or other caregiver can increase a diameter of the lumen, and/or increase a diameter of the second sheath 1502. For example, the clinician or other caregiver could replace an existing second sheath 1502 with a new sheath 1502 having a larger diameter. A clinician or other caregiver could also further open flow through the lumen, by increasing the cross-section of the lumen. For example, as described in relation to FIGS. 1-9, the clinician or other caregiver can selectively increase the cross-section of the lumen by selectively uncovering additional apertures and increasing blood flow from a location upstream of the arteriotomy through the lumen, into the second sheath, and to a location downstream of the arteriotomy.

At least one benefit of the sheath of FIG. 15 and the associated method of FIG. 16 is being able to open a blood flow path between a location upstream of the first arteriotomy to a location downstream of the first arteriotomy (e.g. the second arteriotomy) while only requiring one additional "stick point" or skin puncture 1504—use of the sheath of FIG. 15 and the method of FIG. 16 is safer and simpler than procedures which require additional stick points and more complex equipment, e.g. ECMO. Similarly, at least one benefit of the sheath of FIG. 15 compared to fem-to-fem bypass is the ability to open a blood flow path between a location upstream of the first arteriotomy to a location downstream of the first arteriotomy (e.g. the second arteriotomy) while only requiring one additional "stick point" or skin puncture 1504.

Figure 17:
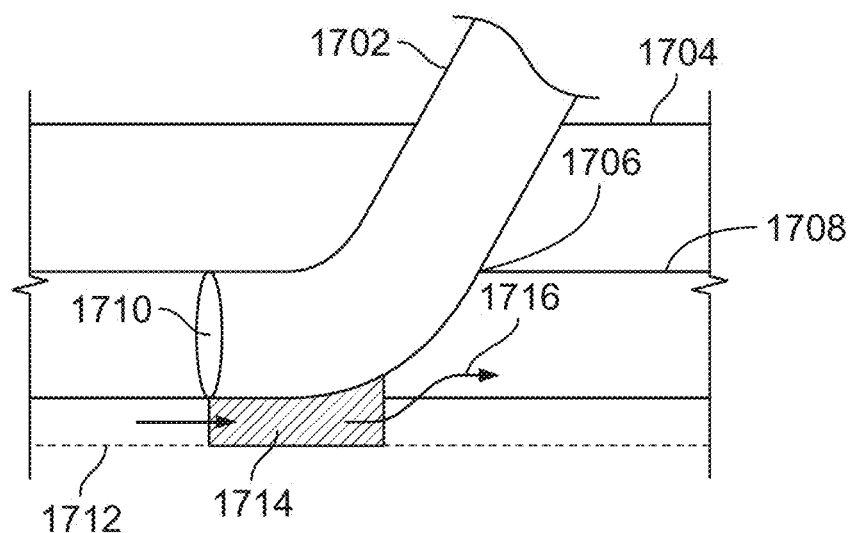
FIG. 17 shows an illustrative view of a sheath with an expandable balloon on an outer surface of a sheath according to an implementation of the present disclosure.

FIG. 17 shows an illustrative view of a sheath with an expandable balloon on an outer surface of a sheath for facilitating downstream perfusion of the patient's vasculature. Sheath 1702 is inserted through the skin 1704 of a patient, and into the artery 1708 of the patient via arteriotomy 1706. Sheath 1702 includes balloon 1714 along at least a portion of the length of the sheath, and on the outer surface of the sheath. When the balloon 1714 is inflated, it separates the outer surface of the sheath 1702 from the wall of the artery 1712 by expanding the artery to a greater diameter locally. The balloon 1714 is sized and shaped to allow for blood flow within the artery, illustrated by arrow 1716 in FIG. 7 from a location upstream of the arteriotomy to a location downstream of the arteriotomy. Exemplary shapes of balloon 1714 are shown and discussed in relation to FIGS. 18A-B below. In one example, a length of the balloon is less than a length of the sheath 1702. In another example, a length of the balloon is less than half a length of the sheath 1702. In one example, when expanded the balloon can form a cylindrical cavity. Alternatively, when expanded the balloon can form a wedge-like cavity, e.g. as shown and discussed below in relation to FIG. 18. Alternatively, in another example the balloon can form a torus. In another example, the balloon 1714 can be any shape forming a channel along the length of the balloon through which fluid can flow.

Balloon 1714 is inflated by inserting an inflating fluid through an inflation lumen connected to the balloon 1714. Such an inflation lumen runs along at least a portion of a length of the sheath body, and has an opening into the balloon cavity located on the outer surface of the sheath. In one example, the inflating lumen is a side-lumen, attached to the outer surface of the sheath body along the length of the inflating lumen. In another example, the inflating lumen is a lumen located within the sheath body but communicates with the outside of the sheath body through an aperture in the sheath, through which the balloon can be inflated and deployed on the outside of the sheath body. In one example, the balloon is stored inside the inflation lumen and is deployed when inflation fluid is inserted through the inflation lumen. In another example, the balloon is stored at a distal end of the inflation lumen, and is deployed when inflation fluid is inserted through the inflation lumen.

Figure 18A:
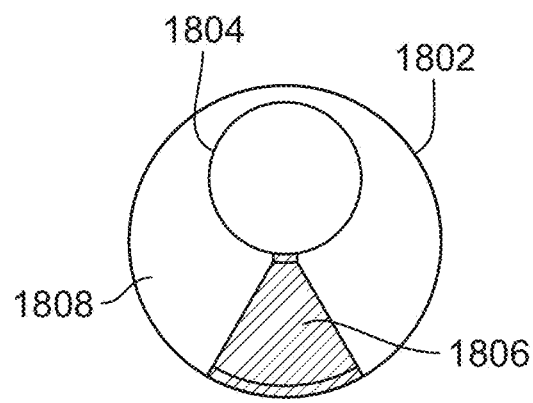
FIGS. 18A-B show illustrative cross sections of a sheath with an expandable balloon an outer surface of a sheath according to an implementation of the present disclosure.
Figure 18B:
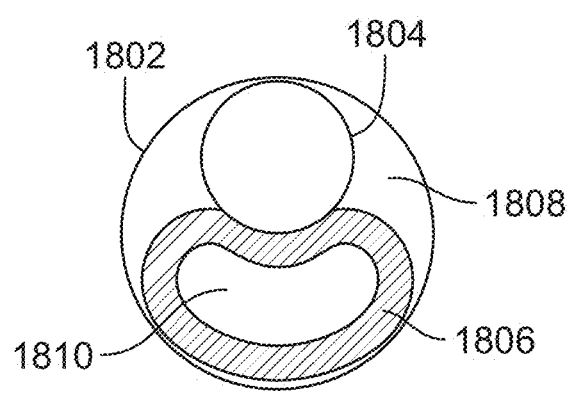

FIGS. 18A-B show illustrative cross sections of a sheath 1804 with an expandable balloon 1806 on an outer surface of a sheath according to an implementation of the present disclosure. FIGS. 18A-B show balloon 1806 inflated. In FIG. 18A balloon 1806 is shaped with a relatively triangular cross-section, taking up less than 360 degrees around the sheath 1804, instead leaving a gap 1808 between the sheath 1804 and the vessel wall 1802 where the balloon is not located. Similarly, in FIG. 18B, balloon 1806 is expanded and leaves gaps 1808 and 1810 between the sheath and the wall of the vessel. Depending on the inflation level or shape of balloon 1806 (shown as a torus in FIG. 18B), blood can flow through gap 1808, gap 1810, or a combination of both. In one example, the type of balloon is selected based on the patient geometry and procedure characteristics. At least one advantage of using a balloon as discussed in relation to FIGS. 17 and 18A-B is the ability to expand the vessel locally and temporarily to open a flow path for blood to flow from a location upstream of the arteriotomy to a location downstream of the arteriotomy.

Figure 19:
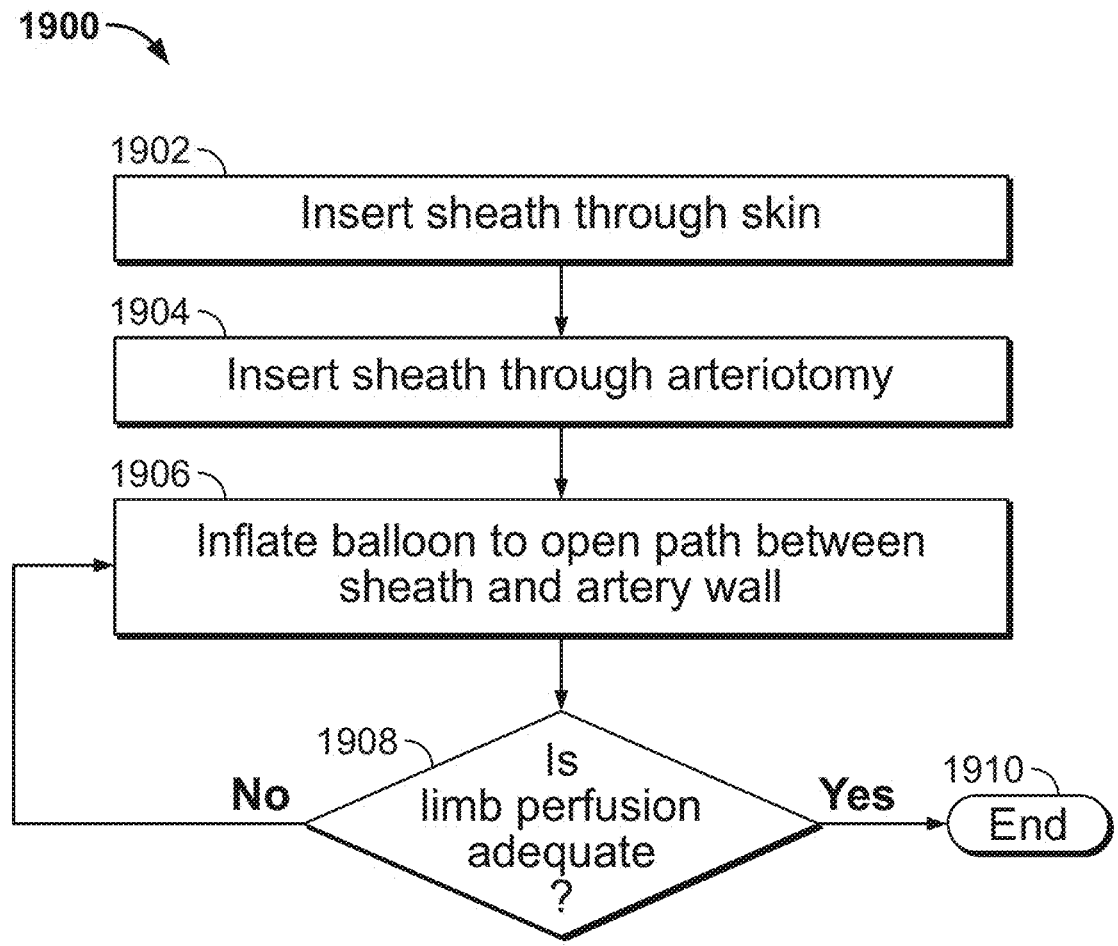
FIG. 19 shows an illustrative method for providing adequate limb perfusion using the sheaths of FIG. 17 or 18A-B.

FIG. 19 shows an illustrative method for providing limb perfusion using the sheaths of FIG. 17 or 18A-B. Process 1900 begins at step 1902 with a clinician or other caregiver inserting the sheath through the skin of a patient. At step 1904 the clinician or other caregiver inserts the sheath through an arteriotomy into the artery of the patient. At step 1906, the clinician or other caregiver inflates the balloon to open up a path between the sheath and a wall of the artery. The clinician or other caregiver checks whether limb perfusion is adequate (step 1908). If the clinician or other caregiver determines that limb perfusion is adequate (step 1908), no action is needed from the clinician or other caregiver to further open up a blood flow path (step 1910). If instead at step 1908, the clinician or other caregiver determines that limb perfusion is not adequate, the clinician or other caregiver further inflates the balloon (step 1906) to widen the path through which blood can flow between the sheath body and the wall of the artery. The clinician or other caregiver can also deflate the balloon when desired to avoid unnecessary radial stress on the artery. In one example, the clinician or other caregiver inflates the balloon beyond a threshold pressure above which the balloon changes shape, providing a blood flow path which is larger and better adapted to a particular patient geometry or characteristics of the procedure.

Figure 20:
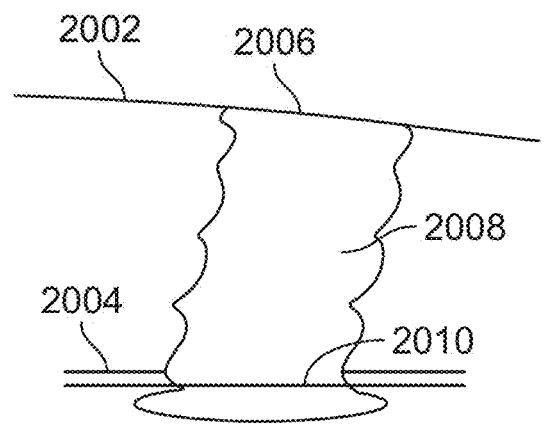
FIG. 20 shows an illustrative cross-section of a conventional system for sealing an access site using collagen.

FIG. 20 shows an illustrative cross-section of a conventional system for sealing an access site using collagen. Patient skin 2002 has a puncture site 2006 propagated through a space between skin surface 2002 and artery 2004, with arteriotomy 2010. To prevent bleeding through the arteriotomy and between the arteriotomy and to the skin, a conventional way to seal the access site is to inject collagen 2008 to fill any space between the skin puncture 2006 and the arteriotomy 2008, thereby sealing the arteriotomy. Patient geometries can vary greatly, with distances between the arteriotomy and the skin puncture ranging between about 2 cm in some patients to about 15 cm in some patients. Moreover, depending on the procedure and the clinician or other caregiver, insertion angles may vary, further contributing to the varying distance to be covered by a sheath to reach the artery.

Figure 21:
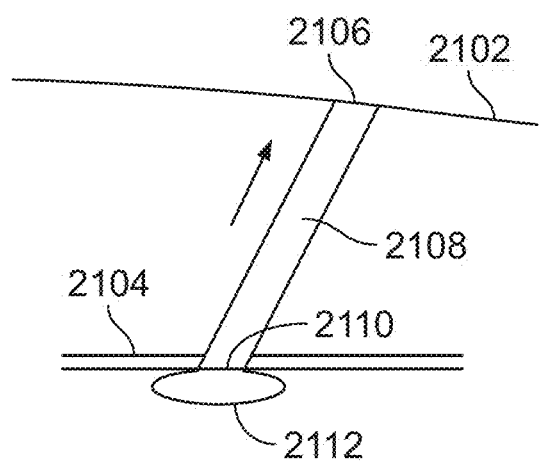
FIG. 21 shows an illustrative cross-section of a sheath system to provide an arteriotomy datum according to an implementation of the present disclosure.

FIG. 21 shows an illustrative cross-section of a sheath system to provide an arteriotomy datum according to an implementation of the present disclosure. Skin 2102 of the patient has a puncture site 2106 through which sheath 2108 can be introduced. Sheath 2108 extends through puncture site 2106 and into the artery 2104 via an arteriotomy. At its distal end, sheath 2108 includes a closure device 2110, shown deployed in FIG. 21, extending over the arteriotomy. At least one benefit of the sheath system of FIG. 21 is the ability to adjust a distance between the artery and the skin, and accordingly a distance between the arteriotomy and the skin puncture, providing a useful datum for a clinician or other caregiver to use later in the procedure. At least another benefit of the sheath system of FIG. 21 is the ability to have a fixed distance between the skin puncture and the arteriotomy, set to no longer be dependent on patient geometry.

Figure 22:
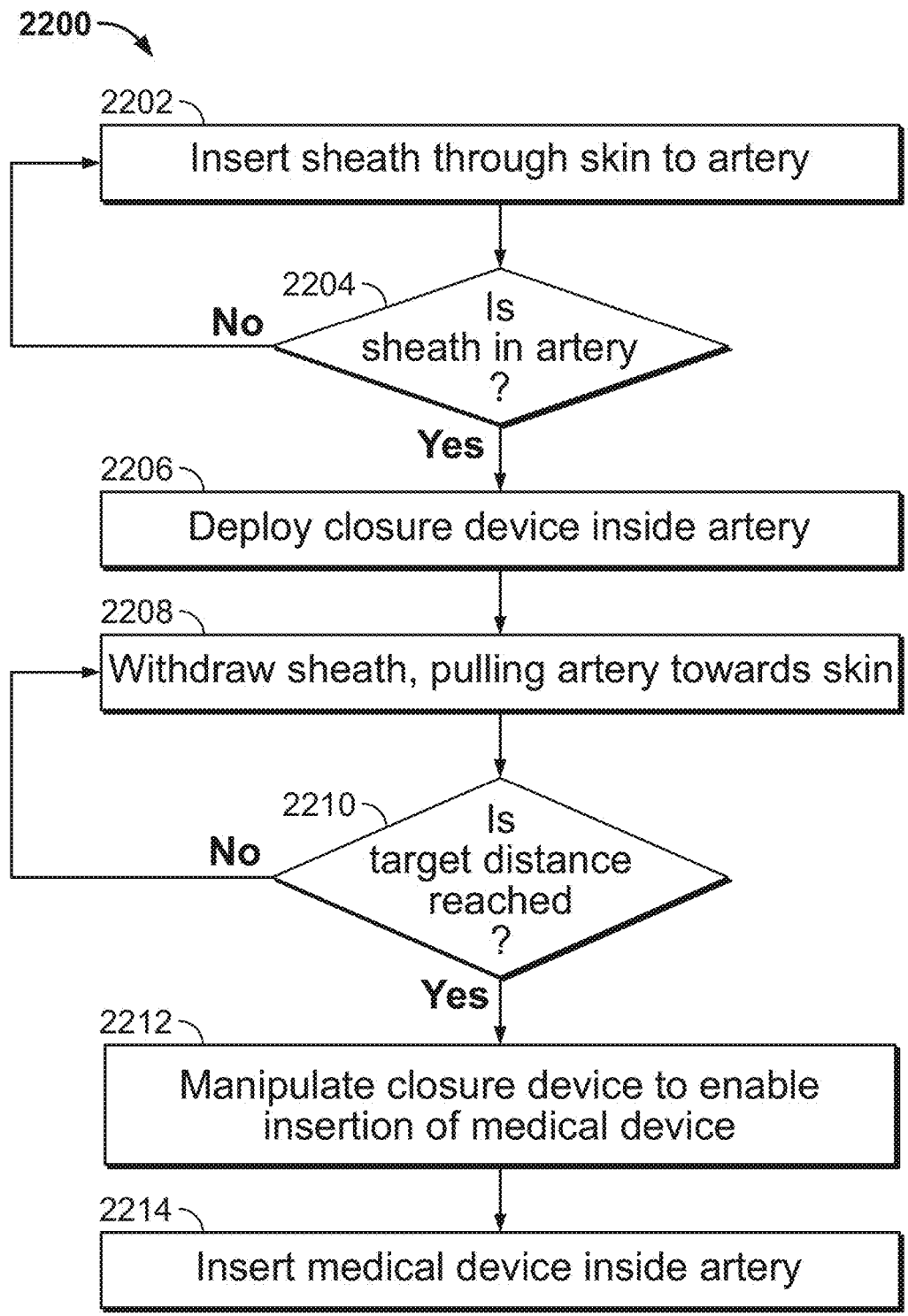
FIG. 22 shows an illustrative method to provide an arteriotomy datum using the sheath system of FIG. 21.

FIG. 22 shows an illustrative method to provide an arteriotomy datum using the sheath system of FIG. 21. Process 2200 begins at step 2202 when a clinician or other caregiver inserts a sheath through the skin of a patient and into the artery. At step 2204 the clinician or other caregiver checks whether the sheath has reached the artery. If not, the clinician or other caregiver continues to insert the sheath before returning to step 2204. If instead the clinician or other caregiver determines that the sheath is in the artery, i.e. an arteriotomy has been made in the artery, and a distal end of the sheath is inside the artery while a proximal end of the sheath is out of the patient skin, process 200 proceeds to step 2206 where the clinician or other caregiver deploys a closure device inside the artery. At step 2208 the clinician or other caregiver withdraws the sheath, with the closure device pulling the artery closer towards the skin, reducing a distance between the artery and the skin, and more specifically reducing a distance between the arteriotomy and the skin puncture.

At step 2210 the clinician or other caregiver checks whether a target distance between the arteriotomy and the skin puncture has been reached. For example, the clinician or other caregiver can reduce the distance between the arteriotomy and the skin puncture until the clinician or other caregiver feels an increased resistance indicative of the closure device being in contact with the access site, and subsequently move the closure device away from the skin puncture by an amount equal to the target distance. For example, a target distance may be between about 5 cm and about 10 cm. In another example, a target distance may be between about 8 cm and about 9 cm. In another example, the target distance may be set by a clinician or other caregiver, or set by standard. If at step 2210 the clinician or other caregiver determines that the target distance between the arteriotomy and the skin puncture has not been reached, the clinician or other caregiver returns to step 2208 and continues to withdraw the sheath. If instead the clinician or other caregiver determines that a target distance has been reached, process 2200 proceeds to step 2212 where the clinician or other caregiver manipulates the closure device to enable insertion of a medical device. In one example, between steps 2210 and 2212 the clinician or other caregiver can tend to other aspects of the procedure. Alternatively, a clinician or other caregiver can step out and a second clinician or other caregiver can step in—the second clinician or other caregiver can use the target distance to quickly carry on with the procedure. At step 2214, the clinician or other caregiver inserts the medical device through the sheath and into the artery. In one example, step 2214 may be replaced a removal of the closure device, and the closing of the access site, in the event that the procedure is indefinitely interrupted, or terminated. As indicated above in relation to FIG. 21, at least one of the advantages of method 2200 is the ability to adjust a distance between the artery and the skin, and accordingly a distance between the arteriotomy and the skin puncture, providing a useful datum for a clinician or other caregiver to use later in the procedure, and the ability to have a fixed distance between the skin puncture and the arteriotomy, set to no longer be dependent on patient geometry.

Figure 23:
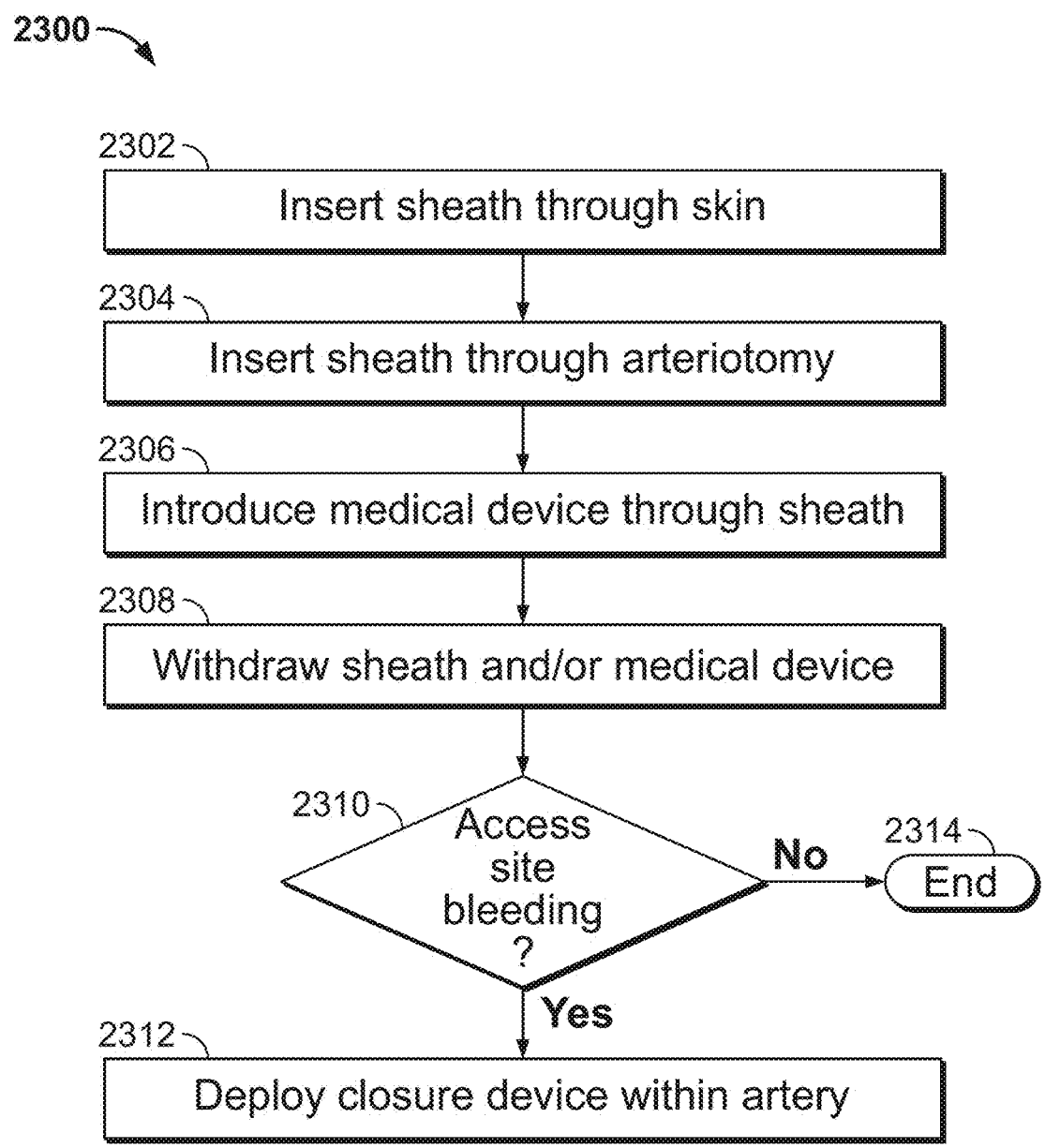
FIG. 23 shows an illustrative method for controlling access site bleeding according to an implementation of the present disclosure.

FIG. 23 shows an illustrative method for controlling access site bleeding according to an implementation of the present disclosure. Process 2300 begins at step 2302 with a clinician or other caregiver inserting a sheath through the skin of the patient. At step 2304 the clinician or other caregiver inserts the sheath into the artery through an arteriotomy. At step 2306 the clinician or other caregiver introduces a medical device through the sheath. After the medical device has been used, at step 2308 the clinician or other caregiver withdraws the sheath or the medical device, or both. After withdrawing the sheath or the medical device or both, the clinician or other caregiver checks for access site bleeding at step 2310. If the clinician or other caregiver determines there is no excessive or undesired access site bleeding at step 2310, the process ends at step 2314.

Otherwise if the clinician or other caregiver does observe excessive or undesired access site bleeding at step 2310, process 2300 proceeds to step 2312 with the clinician or other caregiver deploying a closure device within the artery. If the clinician or other caregiver at step 2308 withdrew only the sheath the closure device being deployed needs to accommodate passage of a catheter or any other elements through the closure device. If the clinician or other caregiver at step 2308 withdrew both the sheath and the medical device, the closure device when deployed does not need to accommodate passage of a catheter or any other elements through the closure device.

At least one advantage of method 2300 is the ability to control access site bleeding either when the sheath has been withdrawn but the medical device or at least a portion of the medical device is still within the patient, or when both the sheath and the medical device have been withdrawn, for example at the end of the procedure. Moreover, at least an additional advantage of method 2300 is the ability to temporarily close access site bleeding while retaining the ability to pass the medical device, and/any other instruments through the closure device. In one example, the closure device is deployed upstream of the arteriotomy. In another example, the closure device is deployed at the arteriotomy. In one example, the closure device is deployed between 30 seconds and 20 minutes. In another example, the closure device is deployed between 30 seconds and 3 minutes.

Figure 24:
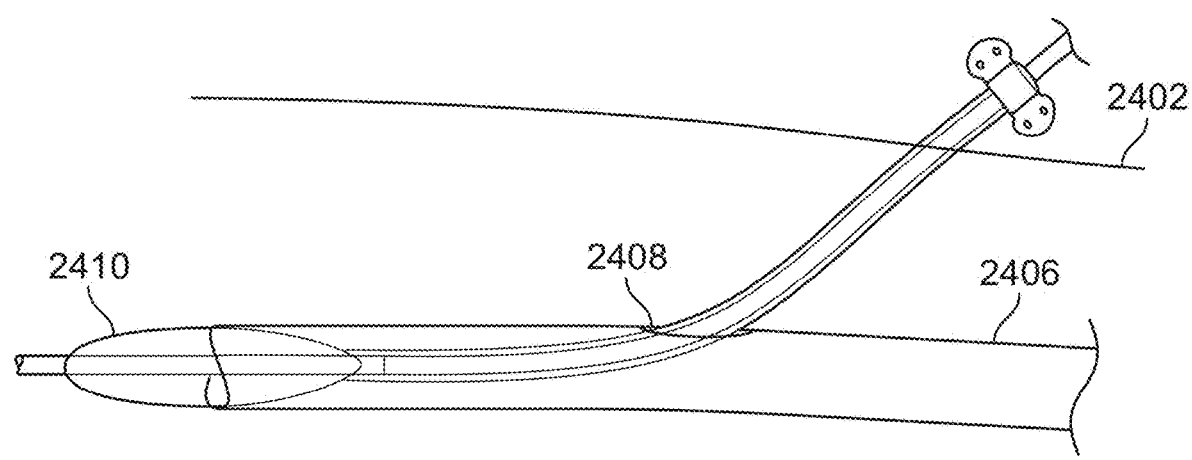
FIG. 24 shows an illustrative view of a closure device deployed upstream of an arteriotomy according to an implementation of the present disclosure.

FIG. 24 shows an illustrative view of a closure device deployed upstream of an arteriotomy according to an implementation of the present disclosure. In the example shown in FIG. 24, closure device 2410 is a balloon, which when expanded blocks or reduces flow of blood from a location upstream of the arteriotomy to a location distal of the arteriotomy. At least one advantage of the closure device 2410 is the ability to tamponade the access site (arteriotomy or skin puncture) to prevent excessive blood loss and allow for closure or other clinical indications or procedures (e.g. attaching a graft to the access site). At least one benefit of the closure device 2410, is that it can be integrated with the sheath assembly, and medical device. Accordingly, whereas existing techniques require a second insertion site with a guidewire and a balloon catheter to be inserted and deployed, requiring additional steps and increased time to control blood flow, the closure device of FIG. 24 and the method of FIG. 25 described below provide a quicker and easier way to temporarily block blood flow. In one example, the closure device can be incorporated onto the sheath assembly, e.g. the sheath assembly described in relation to FIGS. 1-22. In another example, the closure device is incorporated onto the sheath assembly at a fixed location anywhere along the length of the sheath assembly. In another example, the closure device is placed on an external sheath or sleeve (e.g. outer sheath or sleeve 201 in FIG. 5D) which can be moved in a longitudinal direction relative to the sheath assembly and a catheter shaft until the closure device is positioned at a desired location upstream of the arteriotomy. In on example, a shape of the closure device is selected to match an anatomy of the location at which the closure device is to be deployed. For example, a closure device used to block blood flow upstream of an axillary or subclavian arteriotomy is shaped differently than a closure device used to block blood flow upstream of the iliac or femoral artery.

Figure 25:
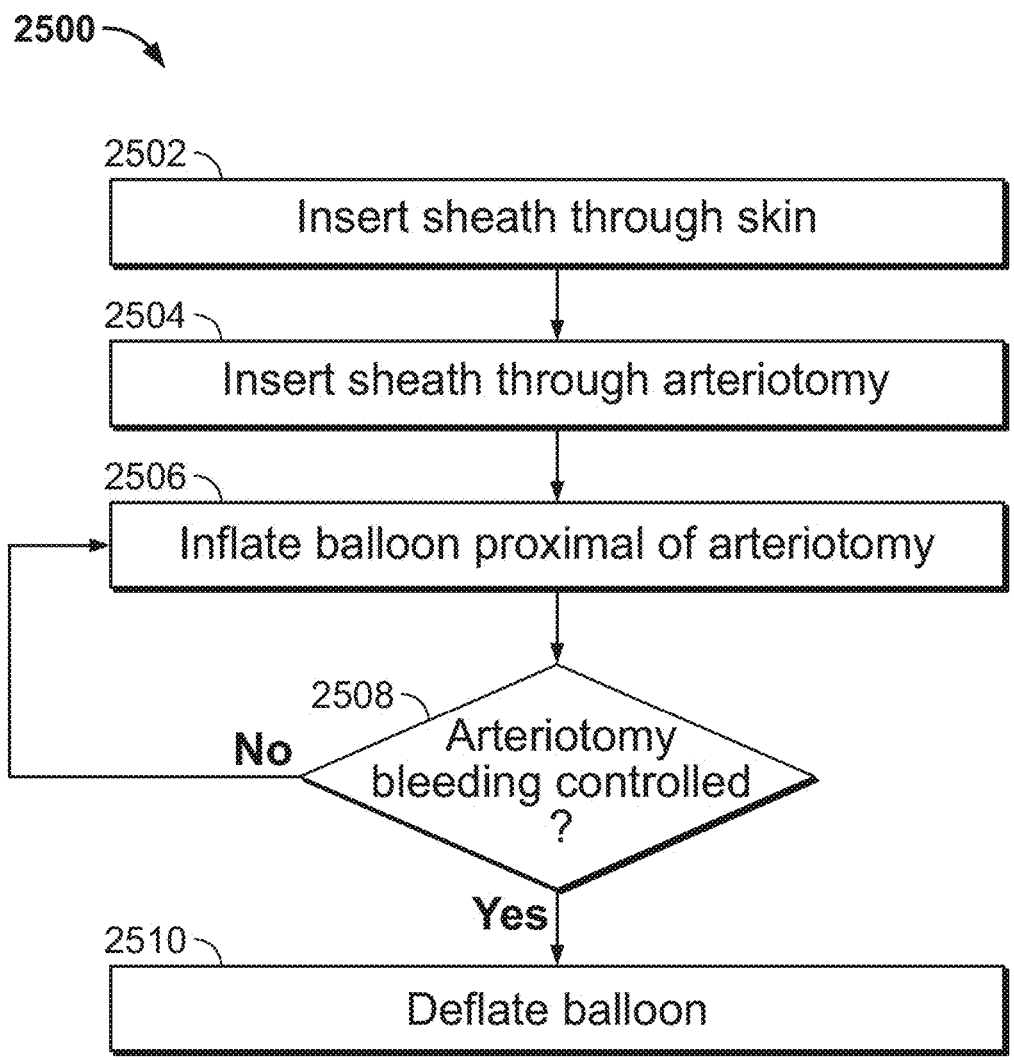
FIG. 25 shows an illustrative method for controlling access site bleeding using the closure device of FIG. 24.

FIG. 25 shows an illustrative method for controlling access site bleeding using the closure device of FIG. 24. In an initial procedure, a clinician or caregiver creates an arteriotomy and percutaneously inserts a sheath through the arteriotomy and into the artery of the patient (steps 2502, 2504). Additional steps may be performed by the clinician or caregiver between the puncture and the arteriotomy on one hand, and insertion of the sheath through the puncture and the arteriotomy on the other hand. For example, the clinician or other caregiver uses a guidewire, and successive dilators to gradually enlarge both the puncture and the arteriotomy sufficiently to accommodate the sheath, which can be an introducer sheath or a repositioning sheath. The sheath is advanced until its distal end is positioned within the artery and the proximal end of the sheath is positioned outside the patient. The clinician or other caregiver can then insert the medical device through the sheath and run the medical device as part of a procedure. During the procedure, the clinician or other caregiver notices undesirable or excessive bleeding at the access site, occluding the access site, and creating a risk of the patient. The clinician or other caregiver then inflates a balloon upstream of the arteriotomy (step 2506). After initial inflation of the balloon upstream of the arteriotomy, the clinician or other caregiver determines whether the arteriotomy bleeding is controlled (step 2508). For example, the clinician or other caregiver can consider the bleeding controlled if the access site is visible, or if the bleeding is reduced. After a sufficient amount of time, the clinician or other caregiver can proceed to deflate the balloon (step 2510). For example, a sufficient amount of time is the amount of time required for the patient to start clotting at the access site. For example the clinician or other caregiver may elect to inflate the balloon, blocking blood flow upstream of the arteriotomy and stopping an unexpected hematoma for 30 minutes until the underlying issue having cause the hematoma can be identified. Once identified and addressed, the clinician or other caregiver can deflate the balloon, ensuring the patient's distal limb still receives adequate blood flow to prevent ischemia. In another example, a sufficient amount of time is the amount of time needed for the clinician or other caregiver to carry out another procedure (e.g. a graft). Alternatively, if more time is necessary, or if the clinician or other caregiver instead determines the arteriotomy bleeding has not been controlled sufficiently, the clinician or other caregiver can further inflate the balloon and later reconsider whether the balloon is sufficiently inflated to provide the desired blood flow control.

Compared to conventional techniques which require the access site to be surgically opened up at the skin level to expose enough vessel to clamp or tie around it (which is particularly difficult in a catheter lab environment), method 2500 provides user the ability to tamponade the vessel upstream of the access site, inside the vessel. The clinician or other caregiver can inflate the balloon and adjust the balloon inflation to control blood flow without requiring the user to cut open the skin beyond the puncture nor requiring the user to remove the blood pump. At least one benefit of method 2500 is the ability to briefly tamponade upstream of the arteriotomy, e.g. to attach a pump to a graft without the patient experiencing extreme blood loss. The closure device used as described in FIG. 25 may be any of the closure devices described in relation to FIGS. 23-28AB. Another exemplary benefit of method 2500 is that the temporary tamponade created by deploying the closure device (e.g. balloon) upstream of the arteriotomy allows the patient to continue to be on hemodynamic support while the access site bleeding/oozing is stopped. The temporary tamponade may promote clotting at the access site, solving bleeding and oozing difficulties and allowing a previously inserted medical device (e.g. blood pump) to remain in place instead of having to be precipitously removed.

Figure 26:
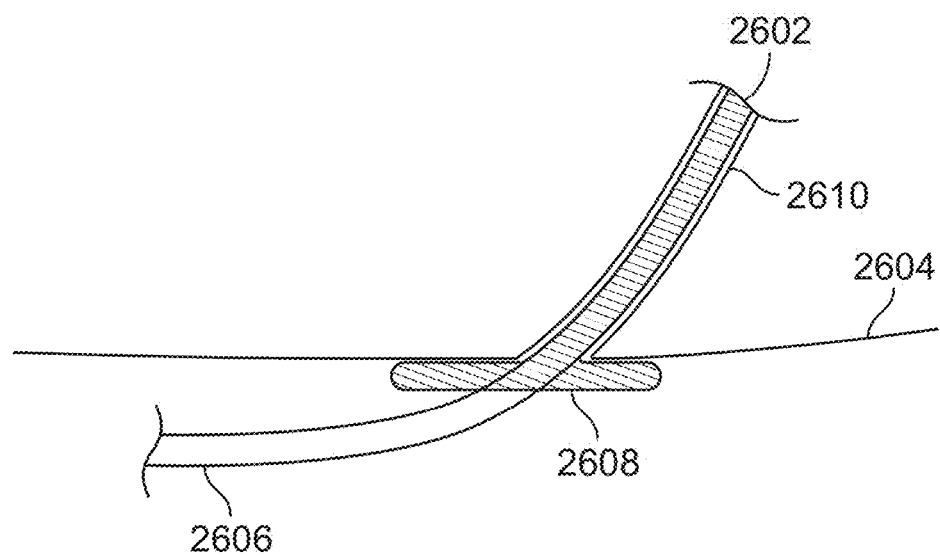
FIG. 26 shows an illustrative closure device for controlling access site bleeding according to an implementation of the present disclosure.

FIG. 26 shows an illustrative closure device for controlling access site bleeding according to an implementation of the present disclosure. A clinician or other caregiver inserts sheath 2610 through a skin puncture 2602 and into artery 2604, for example as described in relation to any of FIGS. 11, 12, 14, 16, 19, 22, 23 and 25. Sheath 2610 includes a distal portion 2608, represented as a footplate in FIG. 26. In the example of FIG. 26 the footplate 2608 is deployed and extends longitudinally in a direction of the artery, surrounding the arteriotomy to occlude it. In one example, the footplate comprises one or more flaps which can pivot about an axis to transition from a compressed state to an expanded or deployed state. In another example, the footplate is a balloon. In one example, the footplate can be a torus shaped balloon. In another example, the footplate can comprise more than one balloon. For example, the footplate can be made of multiple inflatable balloons which extend radially outward. Alternatively, the footplate can comprise both a balloon and a mechanical plate. The footplate is made of Nitinol or synthetic rubber or elastomer. As shown in FIG. 26 a device 2606 can still pass through the closure device 2608 as needed. An opening is present in the center of the closure device. In one example, the opening is smaller than the access site. In another example, the opening is filled by a one-way device such as a flap, or a one-way valve. At least one benefit of the closure device of FIG. 26 is the ability to control blood through the arteriotomy without requiring the user to cut open the skin beyond the puncture and retaining the ability to withdraw or insert elements into the patient.

Figure 27A:
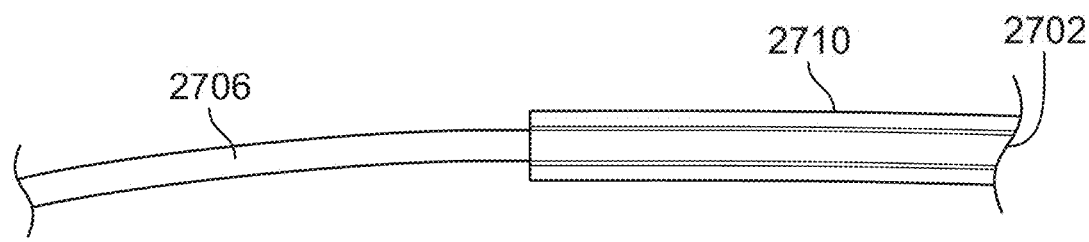
FIGS. 27A-B show an illustrative closure device for controlling access site bleeding before deployment (FIG. 27A), and after deployment (FIG. 27B), according to an implementation of the present disclosure.
Figure 27B:
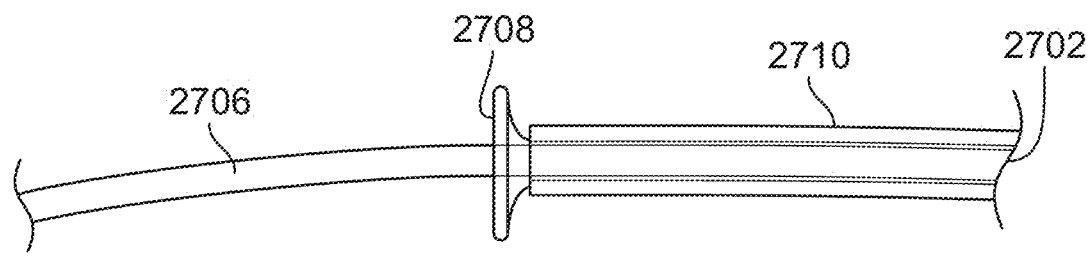

FIGS. 27A-B show an illustrative closure device for controlling access site bleeding before deployment (FIG. 27A), and after deployment (FIG. 27B), according to an implementation of the present disclosure. A clinician or other caregiver inserts sheath 2710 through an arteriotomy 2702, for example as described in relation to any of FIGS. 11, 12, 14, 16, 19, 22, 23 and 25. Sheath 2710 comprises a closure device at its distal portion, the closure device being compressed or retracted within sheath 2710 (and not shown) in FIG. 27A for insertion into the patient. A clinician or other caregiver can exert relative longitudinal motion to unsheath the closure device, or trigger a release mechanism to deploy the closure device. In one example, the closure device comprises flaps which are aligned longitudinally along a length of the sheath, but which deploy when released. In another example, the closure device comprises a balloon, which is deflated during insertion of the sheath 2710, and inflated by the clinician or other caregiver. In the example of FIG. 27B, the sheath 2710 has been retracted such that closure device 2708 is shown deployed at the distal end of the sheath. The clinician or other caregiver can further retract both the sheath and the closure device until the closure device is up against the arteriotomy 2702. At least one benefit of the closure device of FIG. 27 is the ability to control blood flow through the arteriotomy.

Figure 28A:
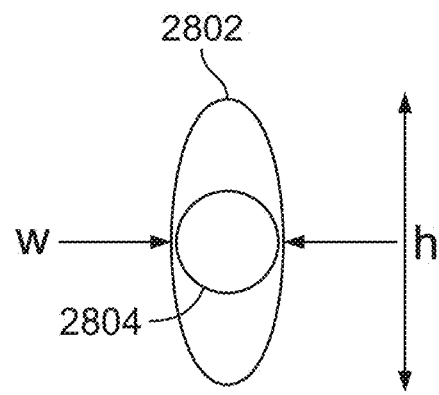
FIGS. 28A-B show an illustrative top view and an illustrative side view of a closure device for controlling access site bleeding according to an implementation of the present disclosure.
Figure 28B:
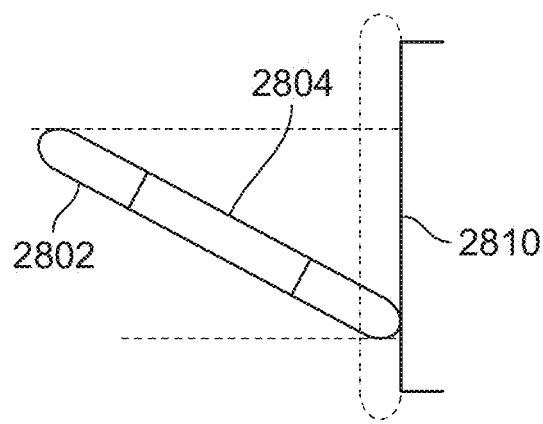

FIGS. 28A-B show an illustrative top view and an illustrative side view of a closure device for controlling access site bleeding according to an implementation of the present disclosure. FIG. 28A shows a footplate type closure device with a width w and height h, having feet 2802 and an opening or flap 2804. The opening or flap 2804 allows insertion of a medical device through the closure device even after the closure device is deployed. FIG. 28 B shows the same footplate type closure device, with opening or flap 2804 and feet 2802. FIG. 28B shows that the closure device can be rotated to such that it can be passed through an opening, such as arteriotomy 2810. In this way, the closure device can be removed from the artery. The closure device of FIGS. 28A-B can be used as described for example in relation to FIGS. 23-27AB. At least one benefit of the closure device of FIGS. 28A-B is the ability to control blood through the arteriotomy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

ILLUSTRATIVE EMBODIMENTS

A1. A method for percutaneously inserting a medical device into a blood vessel of a patient, the method comprising:
 inserting a sheath assembly through a skin puncture into an artery at an arteriotomy, the sheath assembly comprising:
  a sheath body having a longitudinal axis, and first and second ends;
  a first lumen extending along the longitudinal axis between the first and
 second ends of the sheath body;
 inserting the medical device through the first lumen; and
 opening a path through the sheath assembly to allow blood flow from a portion of the artery on a first side of the arteriotomy to a portion of the artery on a second side of the arteriotomy.

A2. The method of A1, wherein opening the path through the sheath assembly comprises moving a cylindrical body relative to the sheath body.

A3. A perfusion sheath assembly for insertion into a blood vessel of a patient, the sheath assembly comprising:
 a sheath body having a longitudinal axis, and first and second ends;
 a first lumen extending along the longitudinal axis between the first and second ends of the sheath body, the first lumen configured to pass a medical device; and
 a second lumen configured to allow blood flow from a portion of the artery on a first side of the arteriotomy to a portion of the artery on a second side of the arteriotomy.

B1. A method for percutaneously inserting a medical device into a blood vessel of a patient, the method comprising:

inserting a sheath assembly through a skin puncture into an artery at an arteriotomy, the sheath assembly comprising:
  a sheath body having a longitudinal axis, and first and second ends;
  a first lumen extending along the longitudinal axis between the first and second ends of the sheath body, the first lumen configured for the passage of a medical device; and
selectively opening and closing one or more openings in the sheath body along the longitudinal axis to allow blood flow from a portion of the artery on a first side of the arteriotomy to a portion of the artery on a second side of the arteriotomy when the first end of the sheath body is positioned within the blood vessel and the second end of the sheath is external to the patient.

B2. A perfusion sheath assembly for insertion into a blood vessel of a patient, the sheath assembly comprising:
  a sheath body having a longitudinal axis, and first and second ends;
  a first lumen extending along the longitudinal axis between the first and second ends of the sheath body, the first lumen configured for the passage of a medical device; and
  a cylindrical body that selectively opens and occludes openings in the sheath body along the longitudinal axis to allow blood flow from a portion of the artery on a first side of the arteriotomy to a portion of the artery on a second side of the arteriotomy when the first end of the sheath body is positioned within the blood vessel and the second end of the sheath is external to the patient.

C1. A perfusion sheath assembly for insertion into a blood vessel of a patient, the sheath assembly comprising:
  a sheath body having a longitudinal axis, and first and second ends;
  first and second lumens, each extending along the longitudinal axis between the first and second ends of the sheath body, the first lumen configured for the passage of a medical device, and the second lumen configured to allow a flow of fluid from the blood vessel in the second lumen; and
  a stylet configured to selectively open and close the second lumen along the longitudinal axis to allow blood flow from a portion of the artery on a first side of the arteriotomy to a portion of the artery on a second side of the arteriotomy when the first end of the sheath body is positioned within the blood vessel and the second end of the sheath is external to the patient.

C2. A method for percutaneously inserting a medical device into a blood vessel of a patient, the method comprising:
  inserting a sheath assembly through a skin puncture into an artery at an arteriotomy, the sheath assembly comprising:
    a sheath body having a longitudinal axis, and first and second ends;
    a first lumen extending along the longitudinal axis between the first and second ends of the sheath body, the first lumen configured for the passage of a medical device; and
    a second lumen extending along the longitudinal axis between the first and second ends of the sheath body, the second lumen configured to allow a flow of blood therethrough; and
  selectively opening and closing openings in the sheath body along the longitudinal axis to by selectively moving a stylet through the second lumen to allow blood to flow from a portion of the artery on a first side of the arteriotomy to a portion of the artery on a second side of the arteriotomy when the first end of the sheath body is positioned within the blood vessel and the second end of the sheath is external to the patient.

D1. A perfusion sheath assembly for insertion into a blood vessel of a patient, the sheath assembly comprising:
  a sheath body having a longitudinal axis, first and second ends, and at least one aperture between the first and second ends;
  a first lumen extending along the longitudinal axis between the first and second ends of the sheath body, the first lumen configured for the passage of a medical device; and
  a sleeve surrounding the sheath body and slidable along the sheath body, to selectively open and close the at least one aperture between the first and second ends when the first end of the sheath body is positioned within the blood vessel and the second end of the sheath is external to the patient.

D2. A method for percutaneously inserting a medical device into a blood vessel of a patient, the method comprising:
  inserting a sheath assembly through a skin puncture into an artery at an arteriotomy, the sheath assembly comprising:
    a sheath body having a longitudinal axis, and first and second ends;
    a first lumen extending along the longitudinal axis between the first and second ends of the sheath body, the first lumen configured for the passage of a medical device; and
    a sleeve surrounding the sheath body; and
  selectively opening and closing openings in the sheath body along the longitudinal axis to by selectively moving the sleeve to allow blood to flow from a portion of the artery on a first side of the arteriotomy to a portion of the artery on a second side of the arteriotomy when the first end of the sheath body is positioned within the blood vessel and the second end of the sheath is external to the patient.

E1. A method for percutaneously inserting a medical device into a blood vessel of a patient, the method comprising:
  inserting a sheath through a skin puncture into an artery at an arteriotomy, the sheath comprising a first portion with a fixed diameter substantially similar to a diameter of the artery and an expandable distal portion;
  expanding the expandable distal portion of the sheath to expand the diameter of the artery to a diameter greater than the fixed diameter of the first portion; and
  inserting the medical device through the sheath and past the expandable distal portion into the artery,
  wherein the expandable distal portion of the sheath is configured to allow blood flow through the artery from upstream of the arteriotomy to downstream of the arteriotomy.

E2. The method of E1, further comprising introducing an anti-clotting agent in the artery.

E3. A perfusion sheath assembly for insertion into a blood vessel of a patient, the sheath assembly comprising:
  a sheath comprising a proximal portion with a fixed diameter substantially similar to a diameter of the blood vessel and an expandable distal portion,
  wherein when the distal portion of the sheath body is expanded and positioned within the blood vessel and at least part of the proximal portion of the sheath is external to the patient, the expandable distal portion of the sheath is configured to allow blood flow through the expanded distal portion from upstream of the arteriotomy to downstream of the arteriotomy, E4. The perfusion sheath assembly of E3 wherein the distal portion is porous.

E5. The perfusion sheath assembly of E4, wherein the distal portion is a mesh.

E6. The perfusion sheath assembly of E5, wherein the distal portion is a stent.

E7. The perfusion sheath assembly of E3, wherein a shape of the expandable distal portion of the sheath when expanded is s-shaped with a first curvature and a second curvature, wherein at least one of the first and the second curvatures are configured such that blood flows through the expanded distal portion from upstream of the arteriotomy to downstream of the arteriotomy.

F1. A method for percutaneously inserting a medical device into a blood vessel of a patient, the method comprising:
    inserting a sheath assembly through a first skin puncture into an artery at a first arteriotomy, the sheath assembly comprising a lumen through which blood can flow;
    inserting a second sheath through a second skin puncture into the artery at a second arteriotomy distal of the first arteriotomy; and
    opening fluid communication between the lumen and the second sheath, such that blood can flow from the lumen through the second sheath and into the artery.

F2. A perfusion sheath assembly for insertion into a blood vessel of a patient, the sheath assembly comprising:
    a first sheath configured for insertion through a first skin puncture into an artery at a first arteriotomy,
    a lumen extending along the first sheath configured to allow blood flow; and
    a second sheath configured for insertion through a second skin puncture into the artery at a second arteriotomy distal of the first arteriotomy,
    wherein the lumen and the second sheath are configured to be in fluid communication such that blood can flow from the lumen through the second sheath and into the artery downstream of the first arteriotomy.

F3. The perfusion sheath assembly of F2, wherein the lumen is integrally formed with the first sheath.

F4. The perfusion sheath assembly of F3, wherein the lumen is concentric with the first sheath.

F5. The perfusion sheath assembly of F4, wherein the lumen is within the first sheath.

F6. The perfusion sheath assembly of F3, wherein the lumen is eccentric from the first sheath.

F7. The perfusion sheath assembly of F6, wherein the lumen is outside of the first sheath.

G1. A method for percutaneously inserting a medical device into a blood vessel of a patient, the method comprising:
    inserting a sheath assembly through a skin puncture into an artery at an arteriotomy, the sheath assembly comprising:
        a sheath body having a longitudinal axis, and first and second ends;
        a first lumen extending along the longitudinal axis between the first and second ends of the sheath body; and
        a balloon coupled to the sheath body; and
    inflating the balloon to open a path between the sheath body and a wall of the artery, wherein blood flows through the path from a portion of the artery on a first side of the arteriotomy to a portion of the artery on a second side of the arteriotomy.

G2. A perfusion sheath assembly for insertion into a blood vessel of a patient, the sheath assembly comprising:
    a sheath assembly configured for insertion through a skin puncture into an artery at an arteriotomy, the sheath assembly comprising:
        a sheath body having a longitudinal axis, and first and second ends;
        a first lumen extending along the longitudinal axis between the first and second ends of the sheath body; and
        a balloon coupled to the sheath body, wherein the balloon when inflated is configured to open a fluid path between the sheath body and a wall of the artery, wherein blood flows through the fluid path from a portion of the artery on a first side of the arteriotomy to a portion of the artery on a second side of the arteriotomy.

G3. The perfusion sheath assembly of G2, wherein the first lumen is integrally formed with the sheath body.

G4. The perfusion sheath assembly of G3, wherein the first lumen is within the sheath body.

G5. The perfusion sheath assembly of G4, wherein the first lumen is eccentric from the sheath body.

G6. The perfusion sheath assembly of G2, wherein the balloon when inflated extends along at least a portion of the sheath body.

G7. The perfusion sheath assembly of G3, wherein a shape of the balloon is configured to open the fluid path.

G8. The perfusion sheath assembly of G7, wherein the balloon surrounds the sheath body over less than 360 degrees, wherein the fluid path between the sheath body and the wall of the artery is around the sheath body where the balloon does not surround the sheath body.

G9. The perfusion sheath assembly of G7, wherein the balloon fully surrounds the sheath body and has a cross-section with an inner channel, wherein the fluid path between the sheath body and the wall of the artery is through the inner channel.

G10. The perfusion assembly of G9, wherein the balloon cross-section is a torus.

H1. A method for percutaneously inserting a medical device into a blood vessel of a patient, the method comprising:
    inserting a sheath assembly through a skin puncture into an artery at an arteriotomy;
    passing a medical device through the sheath assembly; and
    manipulating the sheath assembly to allow flow of blood between a location distal of the arteriotomy and a location upstream of the arteriotomy while simultaneously ensuring hemostasis through the arteriotomy.

H2. The method of H1, wherein manipulating the sheath assembly comprises moving a first component of the sheath assembly relative to a second component of the sheath assembly to create a flow path.

H3. The method of H1, wherein ensuring hemostasis through the arteriotomy comprises deploying a closure device at or distal of the arteriotomy.

H4. A perfusion sheath assembly for insertion into a blood vessel of a patient, the sheath assembly comprising:
    a sheath assembly comprising at least one sheath; at least one lumen; and at least one closure device, wherein the sheath assembly is configured for insertion through a skin puncture into an artery at an arteriotomy, and wherein the sheath assembly is configured to allow flow of blood between a location distal of the arteriotomy and a location upstream of the arteriotomy while simultaneously ensuring hemostasis through the arteriotomy.

H5. The perfusion sheath assembly of H4, wherein the sheath assembly comprises:

a sheath with apertures.

H6. The perfusion sheath assembly of H5, wherein the sheath assembly further comprises a stylet configured to slide within the sheath to open or close the apertures.

H7. The perfusion sheath assembly of H5, wherein the sheath assembly further comprises a sleeve configured to slide around the sheath to open or close the apertures.

H8. The perfusion sheath assembly of H4, wherein the sheath assembly further comprises a closure device.

H9. The perfusion sheath assembly of H8, wherein the closure device is a balloon.

H10. The perfusion sheath assembly of H8, wherein the closure device is a footplate.

I1. A method for percutaneously inserting a medical device into a blood vessel of a patient, the method comprising:

inserting a sheath assembly through a skin puncture into an artery at an arteriotomy, wherein a diameter of the sheath assembly is substantially equal to a diameter of the artery;

passing a medical device through the sheath assembly; and permitting flow of blood between a location distal of the arteriotomy and a location upstream of the arteriotomy while simultaneously ensuring hemostasis through the arteriotomy.

J1. A method for percutaneously inserting a medical device into a blood vessel of a patient, the method comprising:

inserting a sheath assembly through a skin puncture into an artery at an arteriotomy, the sheath assembly including a closure device;

deploying the closure device inside the artery, wherein the closure device provides hemostasis at the arteriotomy;

translating the closure device toward the skin puncture such that a distance between the arteriotomy and the skin puncture is reduced to a target distance;

manipulating the closure device to enable insertion of the medical device into the artery.

J2. The method of J1, wherein manipulating the closure device comprises rotating the closure device such that a cross-section of the closure device is smaller than a cross-section of the arteriotomy.

J3. The method of J2, wherein manipulating the closure device further comprises: temporarily withdrawing the closure device.

J4. The method of J1, wherein manipulating the closure device comprises folding the closure device to a smaller cross-section.

J5. The method of J1, wherein manipulating the closure device comprises deflating the closure device.

J6. The method of J1, further comprising using the target distance to guide insertion of the medical device.

J7. The method of J1, wherein the target distance is identical across a range of patients.

K1. A method for preventing bleeding at an access site for a medical device inserted into a blood vessel of a patient, the method comprising:

inserting a sheath assembly through a skin puncture into an artery at an arteriotomy, wherein the sheath assembly includes a sheath and closure device at a distal end of the sheath; and deploying the closure device from a compressed state to an expanded state, wherein the closure device is located within the artery.

K2. The method of K1, wherein the closure device is a balloon.

K3. The method of K2, further comprising inflating the balloon distal of the arteriotomy.

K4. The method of K2, further comprising inflating the balloon at the arteriotomy to stop blood flow through the arteriotomy.

K5. The method of K1, wherein the closure device is a footplate.

K6. The method of K5, wherein deploying the closure device further comprises displacing the sheath relative to the closure device to deploy the footplate.

L1. A method for preventing bleeding at an access site for a medical device inserted into a blood vessel of a patient, the method comprising:

inserting a sheath assembly through a skin puncture into an artery at an arteriotomy, wherein the sheath assembly includes a sheath and closure device coupled to a distal end of the sheath;

passing a medical device through the sheath into the artery;

withdrawing the sheath from the artery; and deploying the closure device from a compressed state to an expanded state at the arteriotomy to prevent blood flow through the arteriotomy.

L2. The method of L1, wherein the closure device is a balloon, and deploying the closure device comprises inflating the balloon.

L3. The method of L2, wherein when inflated the balloon wraps around a portion of the medical device in the artery.

L4. The method of L3, further comprising adjusting an inflation level of the balloon such that the balloon substantially seals the artery to prevent the blood flow through the arteriotomy.

L5. The method of L1, wherein the closure device is a footplate, and deploying the closure device comprises opening the footplate.

L6. The method of L5, wherein when opened the footplate rests against an inner surface of the artery and occludes the arteriotomy.

L6. The method of L5, wherein when expanded a diameter of the footplate substantially matches a diameter of the artery.

M1. A method for preventing bleeding at an access site for a medical device inserted into a blood vessel of a patient, the method comprising:

inserting a sheath assembly through a skin puncture into an artery at an arteriotomy, wherein the sheath assembly includes a sheath and closure device coupled to a distal end of the sheath;

passing a medical device through the sheath into the artery;

withdrawing the sheath and the medical device from the artery; and deploying the closure device from a compressed state to an expanded state at the arteriotomy to prevent blood flow through the arteriotomy.

M2. The method of M1, wherein the closure device is a balloon, and deploying the closure device comprises inflating the balloon.

M3. The method of M2, further comprising adjusting an inflation level of the balloon such that the balloon substantially seals the artery to prevent the blood flow through the arteriotomy.

M4. The method of M3, wherein when inflated a diameter of the balloon is substantially similar to a diameter of the artery.

M5. The method of M1, wherein the closure device is a footplate, and deploying the closure device comprises opening the footplate.

M6. The method of M5, wherein when opened the footplate rests against an inner surface of the artery and occludes the arteriotomy.

N1. A method for preventing bleeding at an access site for a medical device inserted into a blood vessel of a patient, the method comprising:
 inserting a sheath assembly through a skin puncture into an artery at an arteriotomy, wherein the sheath assembly includes a sheath and closure device coupled to a distal end of the sheath;
 passing a medical device through the sheath into the artery;
 deploying the closure device from a compressed state to an expanded state at a location distal of the arteriotomy to prevent blood flow through the arteriotomy.

N2. The method of N1, wherein the closure device is a footplate, and deploying the closure device comprises opening the footplate.

N3. The method of N2, wherein when opened a diameter of the footplate is similar to an inner diameter of the artery, such that the footplate occludes the artery.

N4. The method of N1, wherein the closure device is a balloon, and deploying the closure device comprises inflating the balloon.

N5. The method of N4, wherein when inflated a diameter of the balloon is similar to an inner diameter of the artery, such that the balloon occludes the artery.

O1. A perfusion sheath assembly for insertion into a blood vessel of a patient, the sheath assembly comprising:
 a sheath body having a longitudinal axis, and first and second ends;
 first and second lumens, each extending along the longitudinal axis between the first and second ends of the sheath body, the first lumen configured for the passage of a medical device, and the second lumen configured to allow a flow of fluid from the blood vessel in the second lumen; and
 a stylet configured to selectively open and close the second lumen along the longitudinal axis when the first end of the sheath body is positioned within the blood vessel and the second end of the sheath is external to the patient.

O2. The perfusion sheath assembly of O1, wherein the stylet is configured to move along the second lumen in order to open and close the second lumen.

O3. The perfusion sheath assembly of O2, wherein the sheath body comprises at least one aperture that enables fluid communication between the second lumen and the blood vessel.

O4. The perfusion sheath assembly of O3, wherein each aperture has a cross sectional area that is similar to that of the second lumen.

O5. The perfusion sheath assembly of O3, wherein the at least one aperture comprises a single continuous channel.

O6. The perfusion sheath assembly of O3, wherein each aperture is configured to prevent the stylet from passing through it into the vessel as it moves along the second lumen.

O7. The perfusion sheath assembly of O1, wherein the stylet comprises an inner lumen that extends along the longitudinal axis between first and second ends of the stylet.

O8. The perfusion sheath assembly of O7, wherein the first end of the stylet comprises a skive.

O9. The perfusion sheath assembly of O7, wherein the inner lumen is exposed at the second end of the stylet.

O10. The perfusion sheath assembly of O7, further comprising an internal stylet for plugging the inner lumen of the stylet when the stylet is not in use.

O11. The perfusion sheath assembly of O7, further comprising a valve at a second end of the stylet for sealing the inner lumen when the stylet is not in use.

O12. The perfusion sheath assembly of O7, further comprising a guidewire that is configured to move along the inner lumen of the stylet.

O13. The perfusion sheath assembly of O2, wherein the stylet comprises markings to indicate the position of the stylet relative to the second end of the sheath body.

O14. The perfusion sheath assembly of O1, further comprising a ratcheting mechanism to retract the stylet towards the second end of the sheath body in standard increments.

O15. The perfusion sheath assembly of O14, wherein the increments are sized relative to a spacing between adjacent apertures.

O16. The perfusion sheath assembly of O1, further comprising a hub coupled to the second end of the sheath body, the hub being in fluid communication with the first lumen.

O17. The perfusion sheath assembly of O16, wherein the hub is also in communication with the second lumen, the hub being configured to receive the stylet.

O18. The perfusion sheath assembly of O1, wherein the sheath body comprises an atraumatic tip attached to the first end of the sheath body.

O19. The perfusion sheath assembly of O18 wherein the tip comprises an inner surface defining a tip lumen that extends between proximal and distal ends of the tip, the tip lumen being in fluid communication with the first and second lumens of the sheath body.

O20. The perfusion sheath assembly of O19, wherein an outer diameter of the proximal end of the tip is larger than an outer diameter of the distal end of the tip such that the tip is tapered.

O21. The perfusion sheath assembly of claim O19, wherein a diameter of the inner surface at the proximal end of the tip is equal to a diameter of the inner surface at the distal end of the tip.

O22. The perfusion sheath assembly of O18, wherein the tip comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%.

O23. The perfusion sheath assembly of O1, wherein the sheath body comprises a first material.

O24. The perfusion sheath assembly of O22, wherein the stylet comprises a second material.

O25. The perfusion sheath assembly of O23, wherein the second material is substantially stiffer than the first material, and the first material is substantially more elastic than the second material.

O26. The perfusion sheath assembly of O22, wherein the first material comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%.

O27. The perfusion sheath assembly of O23, wherein the second material comprises polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, and a material with an elastic modulus of about 40 ksi.

The invention claimed is:

1. A method for inserting a medical device into a patient through a sheath system, the method comprising:
    inserting a sheath assembly into a blood vessel of a patient, thereby creating an arteriotomy, the sheath assembly comprising:
        a sheath body having a longitudinal axis, and first and second ends;
        first and second lumens, each extending along the longitudinal axis between the first and second ends of the sheath body, the first lumen configured for passage of a medical device therethrough, and the second lumen configured to allow a flow of fluid from the blood vessel in the second lumen; and
        a stylet;
    passing a medical device through the first lumen; and
    pulling the stylet to allow blood to flow through the second lumen from a location upstream of the arteriotomy to a location downstream of the arteriotomy.

2. The method of claim 1, further comprising moving the stylet along the second lumen in order to open and close the second lumen.

3. The method of claim 2, wherein the sheath body comprises at least one aperture that enables fluid communication between the second lumen and the blood vessel.

4. The method of claim 3, wherein the at least one aperture has a cross sectional area that is similar to that of the second lumen.

5. The method of claim 3, wherein the at least one aperture comprises a single continuous channel.

6. The method of claim 3, wherein each at least one aperture prevents the stylet from passing through it into the vessel as it moves along the second lumen.

7. The method of claim 1, wherein the stylet comprises an inner lumen that extends along and second ends of the stylet.

8. The method of claim 7, wherein the first end of the stylet a longitudinal axis of the stylet between first comprises a skive.

9. The method of claim 7, wherein the inner lumen is exposed at the second end of the stylet.

10. The method of claim 7, further comprising plugging the inner lumen of the stylet using an internal stylet when the stylet is not in use.

11. The method of claim 7, further comprising sealing the inner lumen when the stylet is not in use using a valve at a second end of the stylet.

12. The method of claim 7, wherein the sheath assembly further comprises a guidewire, the method further comprising moving the guidewire along the inner lumen of the stylet.

13. The method of claim 2, wherein the stylet comprises markings indicating a position of the stylet relative to the second end of the sheath body.

14. The method of claim 1, wherein the sheath assembly further comprises a ratcheting mechanism, the method further comprising retracting the stylet towards the second end of the sheath body in standard increments using the ratcheting mechanism.

15. The method of claim 14, wherein the increments are sized relative to a spacing between adjacent apertures.

16. The method of claim 1, wherein the sheath assembly further comprises a hub coupled to the second end of the sheath body, the hub being in fluid communication with the first lumen.

17. The method of claim 16, wherein the hub is also in fluid communication with the second lumen, the method further comprising the hub receiving the stylet.

18. The method of claim 1, wherein the sheath body further comprises an atraumatic tip attached to the first end of the sheath body.

19. The method of claim 18, wherein the tip comprises an inner surface defining a tip lumen that extends between proximal and distal ends of the tip, the tip lumen being in fluid communication with the first and second lumens of the sheath body.

20. The method of claim 19, wherein an outer diameter of the proximal end of the tip is larger than an outer diameter of the distal end of the tip such that the tip is tapered.

21. The method of claim 19, wherein a diameter of the inner surface at the proximal end of the tip is equal to a diameter of the inner surface at the distal end of the tip.

22. The method of claim 18, wherein the tip comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%.

23. The method of claim 1, wherein the sheath body comprises a first material.

24. The method of claim 23, wherein the stylet comprises a second material.

25. The method of claim 24, wherein the second material is substantially stiffer than the first material, and the first material is substantially more elastic than the second material.

26. The method of claim 23, wherein the first material comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%.

27. The method of claim 24, wherein the second material comprises at least one of: polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, and a material with an elastic modulus of about 40 ksi.

28. The method of claim 1, further comprising determining if limb perfusion is adequate by pulling the stylet thereby allowing blood to flow through the second lumen from a location upstream of the arteriotomy to a location downstream of the arteriotomy.

* * * * *

UNITED STATES PATENT AND TRADEMARK OFFICE
CERTIFICATE OF CORRECTION

PATENT NO.         : 12,233,224 B2
APPLICATION NO.    : 17/964089
DATED              : February 25, 2025
INVENTOR(S)        : Christopher Nason Korkuch et al.

It is certified that error appears in the above-identified patent and that said Letters Patent is hereby corrected as shown below:

In the Claims

Column 37, Line 48, Claim 7:
Now reads: "extends along and second ends of the stylet.";
Should read -- extends along the longitudinal axis between first and second ends of the stylet. --

Column 37, Lines 49-51, Claim 8:
Now reads: "wherein the first end of the stylet a longitudinal axis of the stylet between first comprises a skive.";
Should read -- wherein the first end of the stylet comprises a skive. --

Column 38, Line 51, Claim 27:
Now reads: "comprises at least one of: polyether ether ketone (PEEK)";
Should read -- comprises polyether ether ketone (PEEK) --

Signed and Sealed this
Fifteenth Day of April, 2025

Coke Morgan Stewart
*Acting Director of the United States Patent and Trademark Office*